US011857590B2

(12) United States Patent
Nance et al.

(10) Patent No.: US 11,857,590 B2
(45) Date of Patent: Jan. 2, 2024

(54) SYSTEMS AND METHODS FOR PRODUCING HEMP EXTRACTS AND COMPOSITIONS

(71) Applicant: Ecofibre Limited, Georgetown, KY (US)

(72) Inventors: Alex Nance, Georgetown, KY (US); Geoff D. Ris, Lexington, KY (US); Aaron Jones, Georgetown, KY (US); Lora Lassley, Redondo Beach, CA (US); John Ryan, Carlsbad, CA (US)

(73) Assignee: Ecofibre Limited, Georgetown, KY (US)

( * ) Notice: Subject to any disclaimer, the term of this patent is extended or adjusted under 35 U.S.C. 154(b) by 112 days.

(21) Appl. No.: 18/049,977

(22) Filed: Oct. 26, 2022

(65) Prior Publication Data

US 2023/0131076 A1    Apr. 27, 2023

Related U.S. Application Data

(60) Provisional application No. 63/263,026, filed on Oct. 26, 2021.

(51) Int. Cl.
*A61K 36/185* (2006.01)
*A61K 31/05* (2006.01)

(52) U.S. Cl.
CPC ............ *A61K 36/185* (2013.01); *A61K 31/05* (2013.01); *A61K 2236/31* (2013.01); *A61K 2236/331* (2013.01); *A61K 2236/333* (2013.01); *A61K 2236/35* (2013.01); *A61K 2236/37* (2013.01); *A61K 2236/53* (2013.01); *A61K 2236/55* (2013.01)

(58) Field of Classification Search
None
See application file for complete search history.

(56) References Cited

U.S. PATENT DOCUMENTS

| 10,098,867 | B2 | 10/2018 | Javid et al. |
| 11,123,308 | B2 | 9/2021 | Yu et al. |
| 2021/0069608 | A1 | 3/2021 | Galyuk |
| 2021/0128521 | A1 | 5/2021 | Palaio |

FOREIGN PATENT DOCUMENTS

| CN | 110063953 A | 7/2019 |
| RU | 2745687 C1 | 3/2021 |
| WO | WO/2018/167038 A1 | 9/2018 |
| WO | WO/2019/003163 A2 | 1/2019 |
| WO | WO/2020/163775 A1 | 8/2020 |
| WO | WO/2020/194237 A1 | 10/2020 |
| WO | WO/2021/016718 A1 | 2/2021 |

OTHER PUBLICATIONS

Lazarjani et al. (2021) J. Cannabis Res. 3:32 (15 pages). (Year: 2021).*
International Search Report issued in International Application No. PCT/US2022/078698 dated Dec. 14, 2022.
Fonseca, et al., "Cannabinoid-Induced Cell Death in Endometrial Cancer Cells: Involvement of TRPV1 Receptors in Apoptosis", Journal of Physiology and Biochemistry, vol. 74, No. 2, Feb. 13, 2018, 261-272.
Marinelli, et al., "The Effects of Cannabidiol and Prognostic Role of TRPV2 in Human Endometrial Cancer", International Journal of Molecular Sciences, vol. 21, No. 15, Jul. 29, 2020, 1-22.
Rush, et al., "Cannabidiol: Assessing Activity in Ovarian and Endometrial Carcinoma Cell Lines", Abstracts for the 2021 Society of Gynecologic Oncology 52nd Annual Meeting on Women's Cancer, Featured Posters 188—Poster Session, vol. 162, suppl. 1, Aug. 1, 2021, https://doi.org/10.1016/S0090-8258(21)00839-8.
International Search Report issued in International Application No. PCT/US2022/078691 dated Jan. 30, 2023.
International Search Report issued in International Application No. PCT/US2022/078693 dated Jan. 30, 2023.
Fraguas-Sánchez, et al., "Enhancing Ovarian Cancer Conventional Chemotherapy Through the Combination With Cannabidiol Loaded Microparticles", European Journal of Pharmaceutics and Biopharmaceutics, vol. 154, Jul. 17, 2020, 246-258.
Go, et al., "Cannabidiol Enhances Cytotoxicity of Anti-Cancer Drugs in Human Head and Neck Squamous Cell Carcinoma", Scientific Reports, vol. 10, No. 1, Nov. 26, 2020, 1-11.
Griffiths, et al., "Cannabidiol Suppresses 3-Dimensional Ovarian Cancer Growth and May Enhance Potency of Classic and Epigenetic Therapies", Gynecologic Oncology, vol. 162, suppl. 1, Abstracts for the 2021 Society of Gynecologic Oncology 52nd Annual Meeting on Women's Cancer, Aug. 18, 2021, S102-S103.
Kenyon, et al., "Report of Objective Clinical Responses of Cancer Patients to Pharmaceutical-Grade Synthetic Cannabidiol", Anticancer Research, vol. 38, No. 10, Oct. 1, 2018, 5831-5835.
International Search Report issued in International Application No. PCT/US2022/078701 dated Feb. 15, 2023.
Armour, et al., "Self-Management Strategies Amongst Australian Women With Endometriosis: A National Online Survey", BMC Complementary and Alternative Medicine, vol. 19, No. 1, Jan. 15, 2019, 1-8.

(Continued)

*Primary Examiner* — Russell G Fiebig
(74) *Attorney, Agent, or Firm* — Vos-IP, LLC

(57) ABSTRACT

A method for producing full spectrum hemp extract comprising extracting substances from cannabis-based green material that are soluble in an extraction solvent and collecting an extract that includes the extraction solvent distilling at least a portion of the extraction solvent which results in a concentrate that is not distilled off, removing at least a portion of water soluble substances from the concentrate by partitioning the at least a portion of water soluble substances into an aqueous phase and a remainder of substances from the concentrate into a partitioned concentrate, heating the partitioned concentrate to evaporate the nonpolar solvent and to yield a crude oil, degassing the crude oil by heating it which results in a degassed crude oil, performing a first pass distillation at about 150° C. and collecting a first residue, performing a second and third pass distillation at about 170° C. and about 185° C., and collecting a distillate from same.

15 Claims, 8 Drawing Sheets

(56) References Cited

OTHER PUBLICATIONS

Escudero-Lara, et al., "Disease-Modifying Effects of Natural $\Delta^9$3-Tetrahydrocannabinol in Endometriosis-Associated Pain", eLife, vol. 9, Jan. 14, 2020, https://elifesciences.org/articles/50356.

Ökten, et al., "Cannabidiol as a Potential Novel Treatment for Endometriosis by Its Anti-Inflammatory and Anti-Oxidative Effects in an Experimental Rat Model", Human Reproduction, vol. 37, issue supp. 1, Jun. 30, 2022, i111.

Jaidee, et al., "Kinetics of CBD, $\Delta^9$-THC Degradation and Cannabinol Formation in Cannabis Resin at Various Temperature and pH Conditions", Cannabis and Cannabinoid Research, vol. 7, No. 4, Aug. 9, 2022, 1-11.

Jin, et al., "Identification of Chemotypic Markers in Three Chemotype Categories of Cannabis Using Secondary Metabolites Profiled in Inflorescences, Leaves, Stem Bark, and Roots", Frontiers in Plant Science, vol. 12, Jul. 1, 2021, 1-16.

Marinotti, et al., "Differentiating Full-Spectrum Hemp Extracts from CBD Isolates: Implications for Policy, Safety and Science", Journal of Dietary Supplements, vol. 17, No. 5, Jun. 16, 2020, 517-526.

Rais, et al., "Phytochemicals in the Treatment of Ovarian Cancer", Frontiers in Bioscience-Elite, vol. 9, No. 1, Jan. 1, 2017, 67-75.

Sumanasekera, et al., "Hemp Extract With Specific Anti-Cancer Properties Against Ovarian Cancer", The FASEB Journal Special Issue: Experimental Biology 2021 Meeting Abstracts, vol. 35, No. S1, May 14, 2021, https://doi.org/10.1096/fasebj.2021.35.S1.02877.

* cited by examiner

SYSTEMS AND METHODS FOR PRODUCING HEMP EXTRACTS AND COMPOSITIONS

CROSS-REFERENCE TO RELATED APPLICATIONS

This application claims the benefit of U.S. Provisional Patent Application No. 63/263,026 filed on Oct. 26, 2021, with the United States Patent and Trademark Office, the contents of which are incorporated herein by reference in their entirety.

FIELD OF THE INVENTION

The inventions disclosed herein are related to purification processes and methods of manufacture of cannabis extracts, more particularly to full spectrum hemp extracts (FSHE) and broad spectrum hemp extracts (BSHE) and compositions comprising the same for use in treatment of certain mammalian disorders.

BACKGROUND OF THE INVENTION

The recent delineation of the endocannabinoid system including cannabinoid (CB) receptors (CB1 and CB2) in humans has resulted in an increased interest in therapeutic uses of cannabinoids obtained from plants, or phytocannabinoids. While Δ-9-tetrahydrocannabinol (THC) may be the most notorious phytocannabinoid, cannabidiol (CBD) has gained traction for its therapeutic potential without the adverse psychoactive effects of THC. In fact, in 2019 the World Health Organization (WHO) concluded that CBD posed no public health risk and was virtually absent in causing dependency or addiction.

Within humans, endogenous cannabinoids, or endocannabinoids are naturally produced within the body. The two most well-studied endocannabinoids are anandamide and 2-arachidonoylglycerol (2-AG). Generally, an endocannabinoid acts on one or more CB receptors to cause a cellular response. Alterations of these receptors have been associated with neurogenerative diseases such as Alzheimer's, Parkinson's, and Huntington's diseases. The endocannabinoids, receptors, signaling pathways, and cellular responses are currently being investigated to understand their roles in both normal and disease states.

Phytocannabinoids may act on one or more CB receptors or otherwise influence receptor activation, which is one reason their potential as therapeutics is attractive. Plants that produce cannabinoids include, but are not limited to kava, rosemary, liverwort, electric daisy, echinacea, cacao, helichrysum, pepper trees, black truffles, as well as a strain of yeast (*Pichia pastoris*) with the unique ability to synthesize Δ-9-tetrahydrocannabinolic acid (THCA), which is the precursor to THC. The most well-known cannabinoid producing plants, however, are those belonging to the Cannabaceae family such as those of the *Cannabis* genus. Whether there are distinct species is subject to debate as least two of the identified species, *C. sativa* and *C. indica*, cross breed in nature and by human design. It appears that virtually all *Cannabis* varieties can be considered crosses as plants have been bred to produce a desired profile with regard to biomass and cannabinoid content although many still distinguish plants by species. The U.S. avoids issues of nomenclature by defining hemp as a *Cannabis* plant with a THC content of 0.3% or less by dried weight. The byproducts of hemp plants, including cannabinoids, are federally legal as defined in section 7606 of the 2014 Farm Bill and made permanent in the 2018 Farm Bill.

Regardless of how defined, different strains or varieties of *Cannabis* plants can provide different cannabinoid profiles and growing conditions may affect the resultant cannabinoid profiles of plants within a particular strain. Phytocannabinoids tend to be concentrated in *Cannabis* plants in a viscous resin produced in glandular epidermal outgrowths known as trichomes. The resin is also rich in terpenes, which are largely responsible for the distinct odor of the *Cannabis* plant. Trichomes are most abundant in female inflorescence, but they may be found elsewhere. Furthermore, phytocannabinoid production is not limited to trichomes; they may be produced in other plant structures but nowhere near the same amounts as produced by trichomes.

Chemically, many phytocannabinoids are 21 carbon terpenophenolic compounds obtained by the alkylation of an alkyl resorcinol with a monoterpene unit. A few phytocannabinoids however, do not follow this precise 21-carbon structure. This is primarily due to variation in the length of the sidechain attached to an aromatic ring, which is often a pentyl (5-carbon) or a propyl (3-carbon) chain. To date, over 100 phytocannabinoids have been identified specifically in *Cannabis* plants, and there may more than 144 known phytocannabinoids in all. A few examples of other known phytocannabinoids include Cannabigerol (CBG), Cannabichromene (CBC), cannabidivarin (CBDV), and Cannabinol (CBN). While the purpose of cannabinoids in plants remains unclear, the most popular hypothesis suggests they act to protect the producing plant from insects, bacteria, fungi, ultraviolet radiation, and drying.

Terpenes are a large class of organic compounds produced by a wide number of plants including conifers and leafy plants, such as *Cannabis*. Terpenes often have a strong and readily identifiable odor and are the primary constituent of many essential oils. Thus, the terpenes obtained from many types of plants are used for their aromatic boutique and for other purposes such as certain medicinal properties. Certain terpenes have a chemical profile that is similar to that of cannabinoids and are cannabinoid analogs.

As with many plant-based products, humans do not want to consume large amounts of a plant to obtain the benefit provided particular plant. Thus, to obtain the phytocannabinoids, we have inhaled the smoke of a burned plant. There are a number of negative side effects associated with inhaling the smoke including negative societal implications. Efforts have been made to extract phytochemicals from plants, including phytocannabinoids from hemp plants, to allow the phytochemicals to be taken orally and/or topically instead of inhaled. However, many processes to generate oral and/or topical plant-based products are unregulated and phytochemical extracts may be of varying quality with varying levels of impurities. Such variations are unacceptable if a plant-based product is to be used in treatment of certain medical conditions.

Plant-based extracts and products derived from plant-based extracts require both specific processes for extraction and specific processes for cleansing the plant extract. The specific extraction and subsequent processing produce different final products and different yields. Furthermore, extraction and subsequent processing may also vary depending on the source material used. In order to create end-products from plant-based extracts that have consistent results, all parts of the process from source material to end product are important to obtain product consistency and quality. Notably, certain chemicals used to extract and process phytochemicals can be harmful to a person if ingested. Many of these materials, however, are necessary to extract and to produce sufficient yields of the desired phytochemical.

Because of their natural source, widespread use, low risk of addiction or dependency, and relative safety, CBD and related phytochemicals have been flagged for in-depth investigation of potential therapeutic roles. Applicant has created improved processes to extract and purify one or more cannabinoids from hemp plants; the one or more cannabinoids to be used alone or in pharmaceutical formulations. Such products may be administered orally, topically, via mucosa, and/or other routes of administration to treat a number of mammalian diseases or disorders. The methodologies and extraction processes defined herein provide improvements in yield, reduction in the energy needed to perform the extraction, and improvements in the quality of the resultant products.

SUMMARY OF THE INVENTION

The embodiments here are related to methods for manufacturing and methods for producing a purified BSHE or FSHE, and to produce either the BSHE or FSHE within a pharmaceutically acceptable form.

In a preferred embodiment, a method for producing a full spectrum hemp extract comprising: (a) mixing cannabis-based green material in an extraction solvent of about 5% heptane and about 95% ethanol cooled to between about −20° C. and about 0° C. and collecting an extract that includes the extraction solvent and soluble substances dissolved therein; (b) distilling at least a portion of the extraction solvent off of the extract by heating the extract to a temperature of about 160° F. (about 70° C.) to about 190° F. (about 90° C.) and collecting a concentrate that is not distilled off; (c) removing at least a portion of water-soluble substances from the concentrate by partitioning the at least a portion of water-soluble substances into an aqueous phase and a remainder of substances from the concentrate into a partitioned concentrate dissolved in a phase of a nonpolar solvent; (d) heating the partitioned concentrate to a temperature of about 160° F. (about 70° C.) to about 200° F. (about 95° C.) to evaporate the nonpolar solvent and to yield a crude oil; (e) degassing the crude oil by heating the crude oil to a temperature of about at least 310° F. (about at least 155° C.) in a vacuum that is less than about two torr (less than about 270 Pa), the degassing for a time sufficient to eliminate bubbling of the crude oil, which results in a degassed crude oil; (f) performing a first pass distillation of the degassed crude oil at about 150° C. and collecting a first residue; and (g) performing a second pass distillation of the first residue at between about 170° C. and about 185° C., collecting a second distillate that is a full spectrum hemp extract, and collecting a second residue.

In a further embodiment, the method further comprising performing a third pass distillation on the second residue at a temperature of between about 180° C. and about 190° C., collecting a third distillate that is a full spectrum hemp extract, and combining the second distillate of full spectrum hemp extract and the third distillate of full spectrum hemp extract.

In a further embodiment, the method wherein in step (a) the extract is collected by separating the extraction solvent and soluble substances dissolved therein from any of the cannabis-based green material that is not soluble in the extraction solvent, preferably wherein the separating is carried out by filtration.

In a further embodiment, the method wherein partitioning the at least a portion of water-soluble substances into an aqueous phase and a remainder of substances from the concentrate into a partitioned concentrate dissolved in a phase of nonpolar solvent comprises: (c1) adding about 2 to 5 parts concentrate to about 1 to 5 parts water; (c2) adding about 2 parts to about 5 parts nonpolar solvent to the water and the concentrate; (c3) mixing the water, concentrate, and nonpolar solvent for about 1 minute to about 20 minutes; (c4) letting the mixture sit for at least 30 minutes and optionally up to 180 minutes to allow the aqueous phase and the phase of nonpolar solvent to separate; and (c5) draining the aqueous phase away from the phase of nonpolar solvent to obtain the partitioned concentrate dissolved in a phase of a nonpolar solvent. In a further embodiment, the method wherein: (i) the nonpolar solvent is hexane; and/or (ii) the ratio of water, concentrate, and hexane is about 1 part water, 2 parts concentrate, and 2 parts hexane; and/or (iii) the aqueous phase that was drained away is repartitioned in an equal amount of nonpolar solvent; and/or (iv) collecting the nonpolar solvent and combining the nonpolar solvent with the partitioned concentrate dissolved in a phase of nonpolar solvent.

In a further embodiment, the method further comprising adding fresh extraction solvent after removing the extraction solvent to further extract soluble substances from the same green material and optionally combining the extract from each separate extraction step.

In a further embodiment, the method wherein distilling at least a portion of the extraction solvent off of the extract comprises, when at least 50% of the extraction solvent has been distilled off of the extract, forcing at least a portion of cannabidiolic acid (CBDA) present in the extract to decarboxylate to cannabidiol (CBD) by increasing the temperature to between about 240° F. and 260° F. (between about 115° C. and 130° C.).

In a further embodiment, the method wherein the partitioned concentrate is heated to produce the crude oil in a falling film evaporator and, prior to degassing the crude oil and after visual perception of distillation of the nonpolar solvent has ended, a vacuum of about less than 10 torr (less than 1,350 Pa) is applied to the falling film evaporator for about an hour.

In a further embodiment, the method wherein the degassing step is carried out for from between about 1 minute to about 6 hours, preferably between about 1 minute and 60 minutes.

In a further embodiment, the method wherein the first pass distillation is carried out at a temperature of from 145° C. to 155° C.

In a further embodiment, the method further comprising, dissolving the first residue, the second residue, or both in canola oil at a ratio of 10 parts residue to 1 part canola oil.

In a further embodiment, the method wherein the concentration of CBD in the second distillate, or the combined second distillate and third distillate, of full spectrum hemp extract is between about 70% and about 90%.

In a further embodiment, the method wherein the concentration of Δ9-tetrahydrocannabinol (THC) in the second distillate, or the combined second distillate and third distillate, of full spectrum hemp extract is between about 0.1% and 2.99%.

In a further embodiment, the method wherein the total cannabinoids in the second distillate, or the combined second distillate and third distillate, of full spectrum hemp extract is between about 77% and about 97%.

In a further embodiment, the method wherein the second distillate, or the combined second distillate and third distillate, of full spectrum hemp extract comprises at least one terpene.

In a preferred embodiment, a method for producing a refined broad spectrum hemp extract from a cannabinoid-based extraction product by removal of Δ-9-tetrahydrocannabinol (THC), said method comprising: (a) dissolving the cannabinoid-based extract product in hexane at a ratio of about 2:1 hexane to extract product; (b) formulating a solvent system for centrifugal partition chromatography (CPC) by admixing hexane:methanol:water at a ratio of 5:4:1 respectively; (c) allowing the solvent system to separate for an effective amount of time into an upper layer and a lower layer; (d) adjusting the density of the lower layer to about 0.8 g/cm$^3$ at 70° F. (about 21° C.) using water, methanol, or both; (e) running the dissolved cannabinoid-based extract product through a CPC apparatus to separate the dissolved cannabinoid-based extract product into reclaim fractions, THC-free fractions, and waste fractions; (f) distilling hexane, methanol, water, or combinations thereof from the THC-free fractions in a horizontal wiped film evaporator set to heat at about 140° F. (about 60° C.) and at full vacuum; (g) distilling hexane, methanol, water, or combinations thereof from the THC-free fractions using a rotary evaporator with an oil bath set to at least about 100° C.; (h) removing water from the THC-free fractions using an unheated rotary evaporator under vacuum, a heated rotary evaporator under vacuum, or both; and (i) collecting the resultant broad spectrum hemp extract.

In a further embodiment, the method wherein the concentration of CBD in the broad spectrum hemp extract is between about 79% and about 99%.

In a further embodiment, the method wherein the cannabinoid-based extract product is a full spectrum hemp extract, preferably a full spectrum hemp extract produced by the method.

In a further embodiment, the method wherein a full vacuum is a vacuum of less than 100 torr or about 13.3 kPa.

In a preferred embodiment, a product comprising: (i) a full spectrum hemp extract obtainable by a process or a broad spectrum hemp extract obtainable by the process; and (ii) a fat or an oil; wherein said product comprises between about 1% and 99% of the full spectrum hemp extract or broad spectrum hemp extract. In a further embodiment, the product wherein the fat or oil is a cold pressed hemp seed oil or a medium chain triglyceride (MCT) oil. In a further embodiment, the product wherein the fat or oil is shea butter.

In a preferred embodiment, an oral formulation comprising: (i) between about 0.1% and 30% by weight of a full spectrum hemp extract obtainable by the process or a broad spectrum hemp extract obtainable by the process; (ii) between about 25% and 70% by weight of a medium chain triglyceride (MCT) oil; and (iii) between about 25% and 70% by weight of a cold pressed hemp seed oil.

In a further embodiment, the oral formulation further comprising between about 0.1% and 5% by weight of a terpene blend. In a further embodiment, the oral formulation wherein the terpene blend comprises one or more terpenes selected from the group consisting of: β-myrcene, β-caryophyllene, linalool, α-pinene, citral, D-limonene, eucalyptol, and combinations thereof.

In a further embodiment, the oral formulation further comprising a flavoring agent.

In a further embodiment, the oral formulation further comprising a mucoadhesive agent. In a further embodiment, the oral formulation wherein the mucoadhesive agent is chitosan, hydroxyethyl cellulose, methyl cellulose, polyacrylic acid, poly vinyl pyrrolidone, polyvinyl alcohol, polyethylene glycol, or combinations thereof.

In a preferred embodiment, an intravaginal formulation comprising: (i) between about 0.1% and 50% by weight of a full spectrum hemp extract obtainable by the process or a broad spectrum hemp extract obtainable by the process; and (ii) between about 10% and 90% by weight of a shea butter.

In a further embodiment, the intravaginal formulation further comprising between about 0.1% and 10% by weight of a terpene blend. In a further embodiment, the intravaginal formulation wherein the terpene blend comprises one or more terpenes selected from the group consisting of: β-myrcene, β-caryophyllene, linalool, α-pinene, citral, D-limonene, eucalyptol, and combinations thereof.

In a further embodiment, the intravaginal formulation further comprising between about 5% and 50% by weight of a cold pressed hemp seed oil.

In a further embodiment, the intravaginal formulation further comprising a pH modifier. In a further embodiment, the intravaginal formulation further comprising an osmolality modifier.

In a further embodiment, a system for producing a full spectrum hemp extract comprising: an extractor drum having a mesh screen disposed therein to create a false bottom, the extractor drum configured to contain cannabinoid green material sized to be substantially retained by the mesh screen and prevented from entering the false bottom and an extraction solvent comprising about 5% heptane and about 95% ethanol in which materials extracted from the cannabinoid green material are dissolved and which can collect in the false bottom; a plate heat exchange evaporator configured to receive the extraction solvent and the dissolved materials, the plate heat exchange evaporator having a first set of plate heat exchangers which can be set to between about 160° F. and 190° F. (between about 70° C. and 90° C.) and a pressure of about 5 psi to about 10 psi (about 34 kPa to about 69 kPa) for evaporating the extraction solvent and a second set of plate heat exchangers which can be set at about 70° F. (about 21° C.) for condensing vaporized extraction solvent away from a resultant cannabinoid concentrate; a partition funnel configured to receive the cannabinoid concentrate, water, and hexane in a ratio of about 2:1:2 respectively, such that the cannabinoid concentrate may be partitioned within the partition funnel into water soluble substances dissolved in water and hexane soluble substances dissolved in the hexane; a falling film evaporator for receiving the hexane and hexane soluble substances, the falling film evaporator having a first setting of about 160° F. to about 200° F. (about 70° C. to about 95° C.) for removing the hexane from the hexane soluble substances and a second setting enabling a vacuum pressure of initially about less than 10 torr (less than 1,350 Pa) that can be gradually increased to about 20 torr to 25 torr (about 2,650 Pa to 3,350 Pa), the second setting configured to be set after the hexane is visually assessed as being removed, which after about an hour enables production of a crude oil comprising the hexane soluble substances; a condenser operatively connected to the falling film evaporator which can be set at 50° F. (10° C.) for condensing vaporized hexane; a vacuum oven for receiving the crude oil which can be set at 310° F. (about 155° C.) and under vacuum to degas the crude oil; and at least one wiped film short pass still for producing refined full spectrum hemp extract from the degassed crude oil after at least two sequential passes through the still, the first pass removing terpenes from the crude oil and the second pass producing the full spectrum hemp extract as a distillate.

In a preferred embodiment, use of a system for carrying out a method for producing a full spectrum hemp extract.

In a preferred embodiment, a cannabis extract made by any one of the processes, comprising: between 50 and 95% CBD and between 0.1 and 5% Δ9-THC.

In a further preferred embodiment the cannabis extract comprising at least one additional cannabinoid of between 0.01 to 5.0% selected from the group consisting of: Δ9 tetrahydrocannabinol (Δ9-THC), tetrahydrocannabinolic acid (THCA), tetrahydrocannabivarin (THCV), Δ8 tetrahydrocannabinol (Δ8-THC), cannabichromene (CBC), cannabichromene acid (CBCA), cannabigerol (CBG), cannabigerol acid (CBGA), cannabidiol (CBD), cannabidiolic acid (CBDA), cannabidivarin (CBDV), cannabinol (CBN), Cannabicyclol (CBL), CBDA, and combinations thereof.

In a preferred embodiment, the cannabis extract comprising at least two additional cannabinoids, each at a weight percent of at least 0.1%.

In a preferred embodiment, the cannabis extract comprising between 66 and 95% CBD, at least 0.1 to 5.0% Δ9-THC, and preferably not more than 0.1 to 0.3%; and wherein the total cannabinoids are at least 70% by weight.

In a further embodiment, a product made by the process defined herein, said product comprising between 1 and 99% of a cannabis extract, and wherein the cannabis extract is admixed with a fat or an oil.

In a further preferred embodiment, the product wherein the fat or oil is a cold pressed hemp seed oil or an MCT oil. In a further preferred embodiment, the product wherein the fat or oil is shea butter.

In a further embodiment, an oral formulation comprising: an extract made by any one the processes defined herein comprising between 10 and 90% by weight of the oral formulation and comprising an MCT oil at a concentration of between 0.1 and 10%, and a cold pressed hemp seed oil, each having between 25 and 70% of the total weight of the oral formulation.

In a further preferred embodiment, the oral formulation comprising a flavorant.

DETAILED DESCRIPTION OF THE INVENTION

Figure 1:
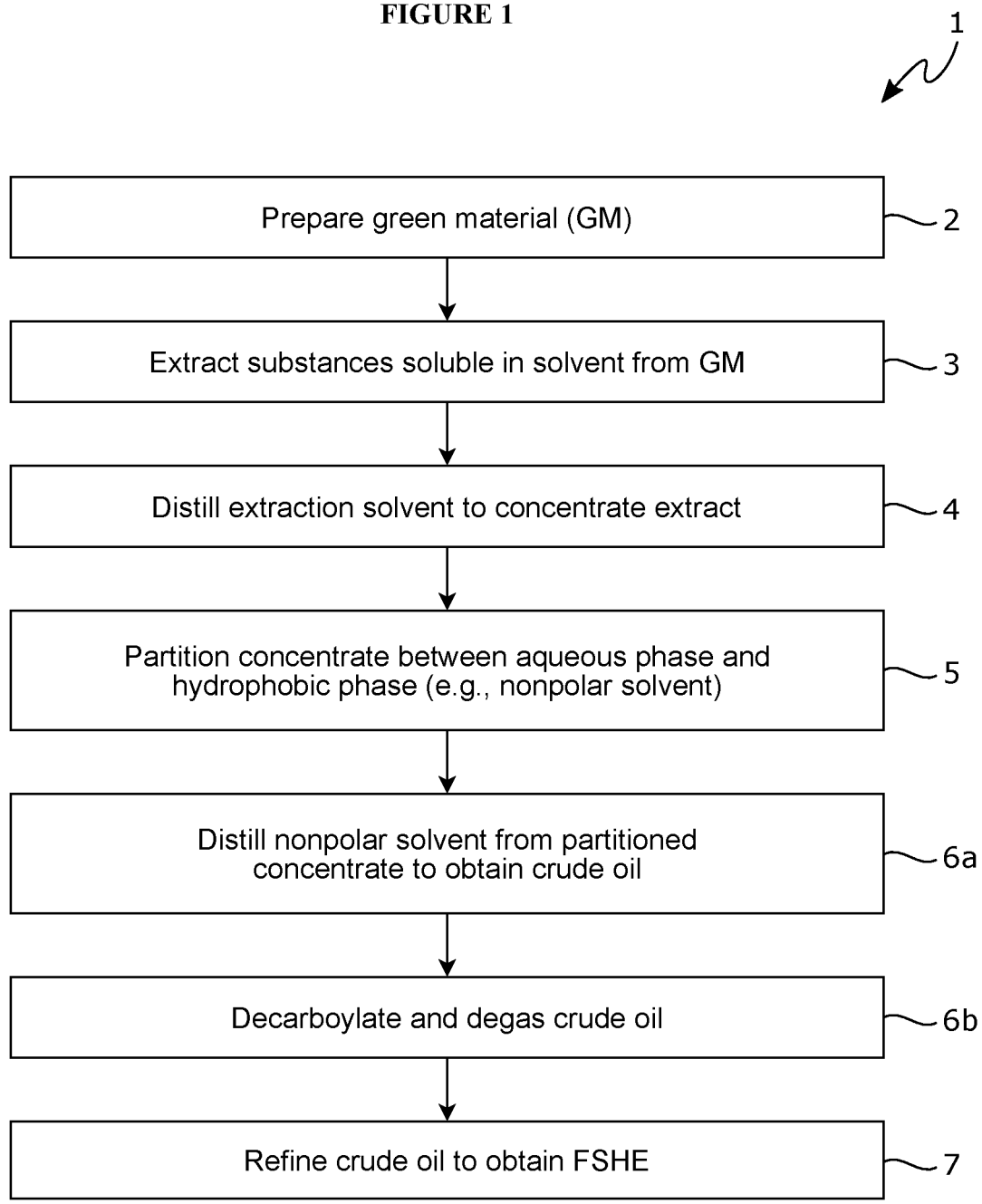
FIG. 1 depicts a flow diagram of steps for extracting and producing a Full Spectrum Hemp Extract (FSHE).

Various embodiments are described more fully hereinafter with reference to the accompanying drawings, which form a part hereof, and which show, by way of illustration, specific exemplary embodiments by which the innovations may be practiced. The embodiments may, however, be embodied in many different forms and should not be construed as limited to the embodiments set forth herein; rather, these embodiments are provided so that this disclosure will be thorough and complete, and will fully convey the scope of the embodiments to those skilled in the art. Among other things, the various embodiments may be methods, formulations, compositions, and the like. The following detailed description is, therefore, not to be taken in a limiting sense.

Definitions

As used herein, the term "about" means plus or minus 5% of the numerical value of the number with which it is being used. Therefore, about 50% means in the range of 45%-55%. As a non-limiting example, a temperature of about 150° C., means a range of 142.5° C. to 157.5° C., inclusive of the endpoints and all numbers therebetween.

"Broad spectrum hemp extract (BSHE)" as used herein BSHE is a composition derived from the *Cannabis* genus of plants which has undergone at least some purification in order to refine the extract. Typically, BSHE comprises between 60 and 99.9% CBD and least one additional cannabinoid, selected from the group consisting of Δ9-THC, THCA, THCV, Δ8-THC, CBC, CBCA, CBG, CBGA, CBDA, CBDV, CBN, CBL, and combinations thereof the sum of which is between 0.1 and 40%.

As used here, the term "cannabis extract" (CE) is a composition derived from the *Cannabis* genus of plants (including hemp). Typically, a cannabis extract contains cannabidiol, and more typically comprises both cannabidiol (CBD) and at least one additional cannabinoid, selected from the group consisting of Δ9-THC, THCA, THCV, Δ8-THC, CBC, CBCA, CBG, CBGA, CBDA, CBDV, CBN, CBL, and combinations thereof at between 0.1 and 40%. Cannabis extracts according to the present invention are typically enriched in cannabidiol, and may comprise between 1 and 99.9% CBD, preferably between 20 and 99.9% CBD, more preferably between 50 and 99.9% CBD, even more preferably between 70 and 99.9% CBD, and most preferably between 90 and 99.9% CBD. Full spectrum hemp extract, broad spectrum hemp extract, CBD isolate, and CBDA isolate are forms of cannabis extract utilized herein, as non-limiting examples of the CE.

"Composition" as used herein is intended to encompass a product comprising the specified ingredients in the specified amounts, as well as any product which results, directly or indirectly, from combination of the specified ingredients in the specified amounts.

"CBD/CBD isolate" as used herein encompasses a purified concentration of CBD molecules to a purity of greater than 98%.

As used herein, the term "full spectrum hemp extract (FSHE)" is a composition derived from the *Cannabis* genus of plants which contains CBD, and quantities of THC above 0, preferably, between 0.01% and 5%, most preferably being between 0.01% and 0.3%. The FSHE may comprise additional cannabinoids, yielding a product that comprises at least 50-99% CBD, at least 0.01% to 10% THC (the sum of Δ9-THC, THCA, THCV, Δ8-THC), and total cannabinoids of between 50% and 99% of the weight of the CE.

"Source material" as used herein encompasses the cannabis plants that are harvested to be used in an extraction process.

"*Cannabis*-based green material" (GM) as used herein encompasses the parts of the source material producing the most cannabinoids including the flowers/inflorescence and some leaf material. Preferably, "cannabis-based green material" refers to inflorescence and leaf material of plants of the *cannabis* genus.

"Extract" as used herein encompasses an extraction solvent and the extracted materials dissolved in the extraction solvent.

"Concentrate/Concentrated extract" as used herein encompasses extracted materials from the extract that remain after the extraction solvent has been removed.

"Partitioned concentrate" as used herein encompasses the materials in the concentrate that are soluble in a nonpolar solvent and result from a partitioning of concentrate between an aqueous phase and the nonpolar solvent.

"Crude oil" as used herein encompasses the resultant oil after hexane from a portioning step has been distilled off.

"Residue" as used herein encompasses the material left behind as a result of distillation, and more particularly the material left behind as a result of a distillation step in a short pass still.

"Distillate" as used herein encompasses the material removed (i.e., which is evaporated and recondensed) in a distillation step, and more particularly the material removed as a result of distillation in a short pass still.

"At least a portion of" as used herein refers to at least 5%, preferably at least 10%, more preferably at least 20%, still more preferably at least 50%, and most preferably at least 75%, for example from 75% to 99%, from 75% to 95%, or from 75% to 90%. Thus, distilling at least a portion of the extraction solvent off of the extract typically means distilling at least 5%, preferably at least 10%, more preferably at least 20%, still more preferably at least 50%, and most preferably at least 75%, for example from 75% to 99%, from 75% to 95%, or from 75% to 90%, of the extraction solvent off of the extract. Similarly, removing at least a portion of water-soluble substances from the concentrate typically means removing at least 5%, preferably at least 10%, more preferably at least 20%, still more preferably at least 50%, and most preferably at least 75%, for example from 75% to 99%, from 75% to 95%, or from 75% to 90%, of the water-soluble substances from the concentrate.

"Nonpolar solvent" as used herein refers to a solvent having a polarity index of 3.5 or less in accordance with the values calculated by Burdick and Jackson (list available at https://macro.lsu.edu/howto/solvents/polarity %20index-.htm). Preferably, the nonpolar solvent is selected from pentane, hexane, heptane, toluene, the fraction of petroleum ether boiling between 30-40° C., the fraction of petroleum ether boiling between 40-60° C., toluene, xylene, diethyl ether and dichloromethane. Most preferably, the nonpolar solvent is hexane.

"THC-free fraction" as used herein is a fraction obtained from centrifugal partition chromatography which contains less than 0.1% or less Δ-9-tetrahydrocannabinol (THC), preferably 0.008% or less, and more preferably less than 0.0027% THC.

"Reclaim fraction" as used herein is a fraction obtained from centrifugal partition chromatography which contains more than 2% Δ-9-tetrahydrocannabinol (THC) and also more than 40% cannabidiol (CBD). Such a fraction can be recycled in the centrifugal partition step in order to obtain more of the desired BSHE product as described herein.

"Waste fraction" as used herein is a fraction obtained from centrifugal partition chromatography which contains 10% or less cannabidiol (CBD) and is either recycled or discarded following the centrifugal partition chromatography step.

Ralph Mechoulam coined the term 'entourage effect' to describe the inexplicable synergy that manifests when multiple naturally occurring compounds extracted from *Cannabis* plants are consumed in tandem. This effect is thought to be the result of multi-pathway activation and signaling from various nutrients in a hemp extract comprising more than just isolated CBD alone.

The Full Spectrum Hemp Extracts (FSHE) resultant from processes described herein include multiple naturally occurring cannabinoids extracted from hemp plants. Such FSHE can also include, without limitation, additional naturally occurring phytonutrients such as essential fatty acids, flavonoids, terpenes, vitamins, and minerals such as, without limitation, omega-3 and omega-6 fatty acids, antioxidants, potassium, magnesium, iron, zinc, calcium, phosphorus, vitamin E, and other molecules. Broad Spectrum Hemp Extracts (BSHE) are produced by removing detectable amounts of THC from the FSHE while retaining other cannabinoids including CBD. BSHE also include some or all of the additional non-cannabinoid phytonutrients that are found in FSHE. Thus, to obtain the benefit of multiple types of cannabinoids plus other naturally occurring phytonutrients, one should use a FSHE or BSHE such as those produced by the processes described herein and not from a CBD isolate, which is only cannabidiol.

Extracting cannabinoids and other phytochemicals from hemp plants is riddled with numerous challenges towards commercial viability of products. Firstly, phytocannabinoids are nearly insoluble in water; thus, they must be extracted using alcohols and/or nonpolar organic solvents. These solvents will also extract many impurities and other undesirables in addition to the desired molecules. The impurities, undesirable molecules, and solvents all need to be separated and removed from the desired cannabinoids and phytonutrients, which can be complicated, time consuming, and expensive. Some processes are insufficient in removal capabilities leaving impurities and sometimes harmful substances in their resultant extract. Conversely, in an effort to produce a quality product, other processes may remove many desired cannabinoids and phytonutrients in addition to the impurities etc. Either way, many of these processes were time consuming and suffered from inconsistent cannabinoid profiles between batches. Furthermore, many production processes ended with unsustainably low yields, leading to high prices for the generated extraction product oil.

Applicant has discovered improved ways to extract cannabinoids and other phytonutrients from hemp plants and to purify such extractions via systems and processes that are more efficient, generate greater yields of desired key compounds, increase the diversity of desirous cannabinoids, terpenes, and other molecules found in the extractions, and providing greater consistency of the final product. The resultant high quality FSHE and BSHE are suitable for both personal and pharmaceutical use.

Although our previous process worked well, it could be improved, especially with respect to throughput. Per the prior process, cannabinoids and other phytonutrients were extracted from frozen GM using ethanol as a solvent. Ethanol was removed from the extracted materials using a horizontal wiped evaporator. The result of ethanol removal was a black tarry substance, which upon distillation yielded hemp oils. The black tarry substance clung to glassware and other equipment, was difficult to work with, and removal oftentimes caused damage to glassware and equipment with physical removal. In fact, it could take up to two weeks to clean the substance from glassware and other equipment as compared to extraction/purification, which took about one day. Furthermore, yield was incomplete as cannabinoids, etc. were lost in the black tarry substance that was left behind on the glassware/equipment. Thus, the prior process could be improved at least because of the high running costs of materials and the time needed for cleaning between processing one batch of GM to then next, but also by dramatically increasing the yield.

Figure 2:
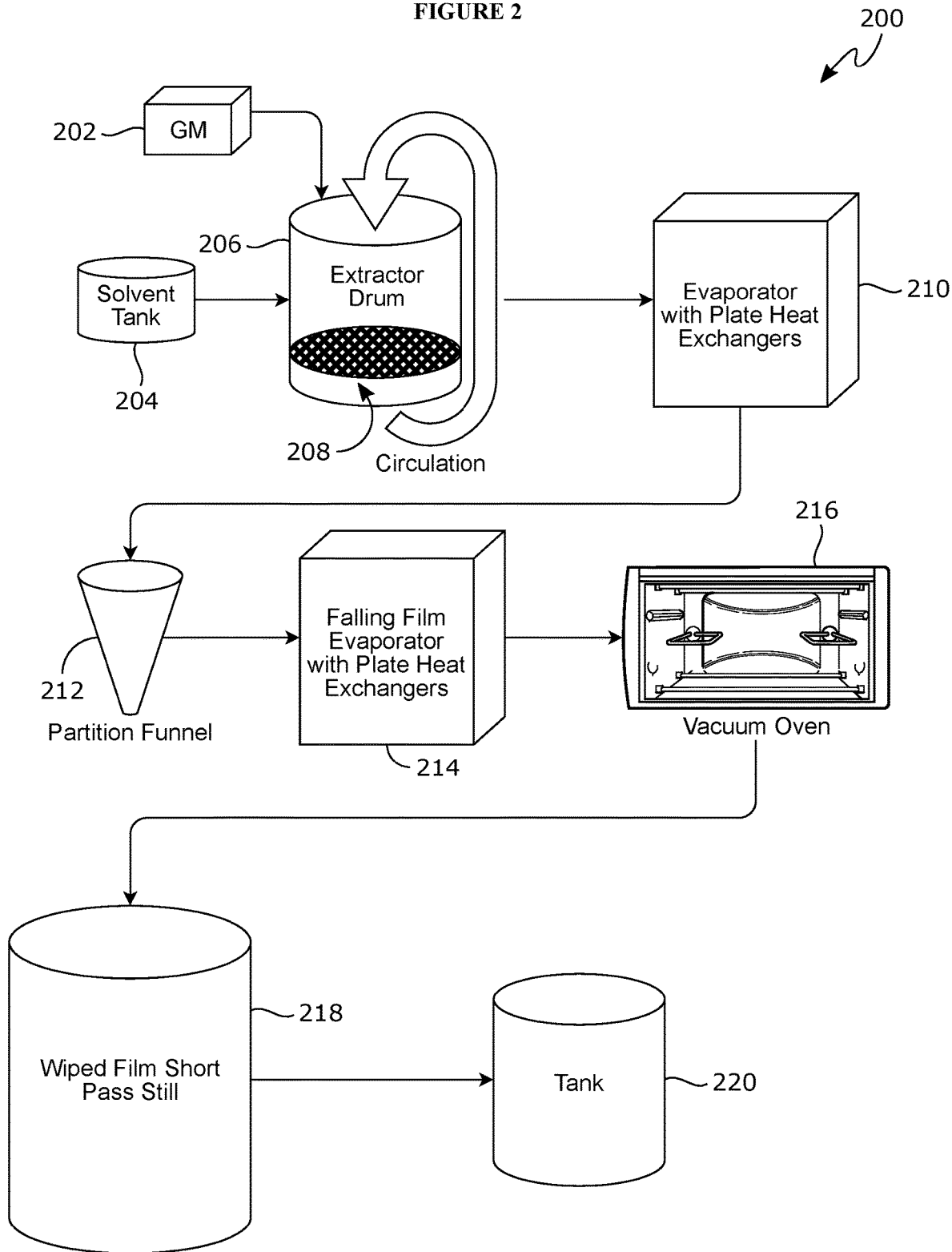
FIG. 2 depicts a combination block diagram and flow diagram of an exemplary system which may be utilized to perform the method of FIG. 1.
Figure 8:
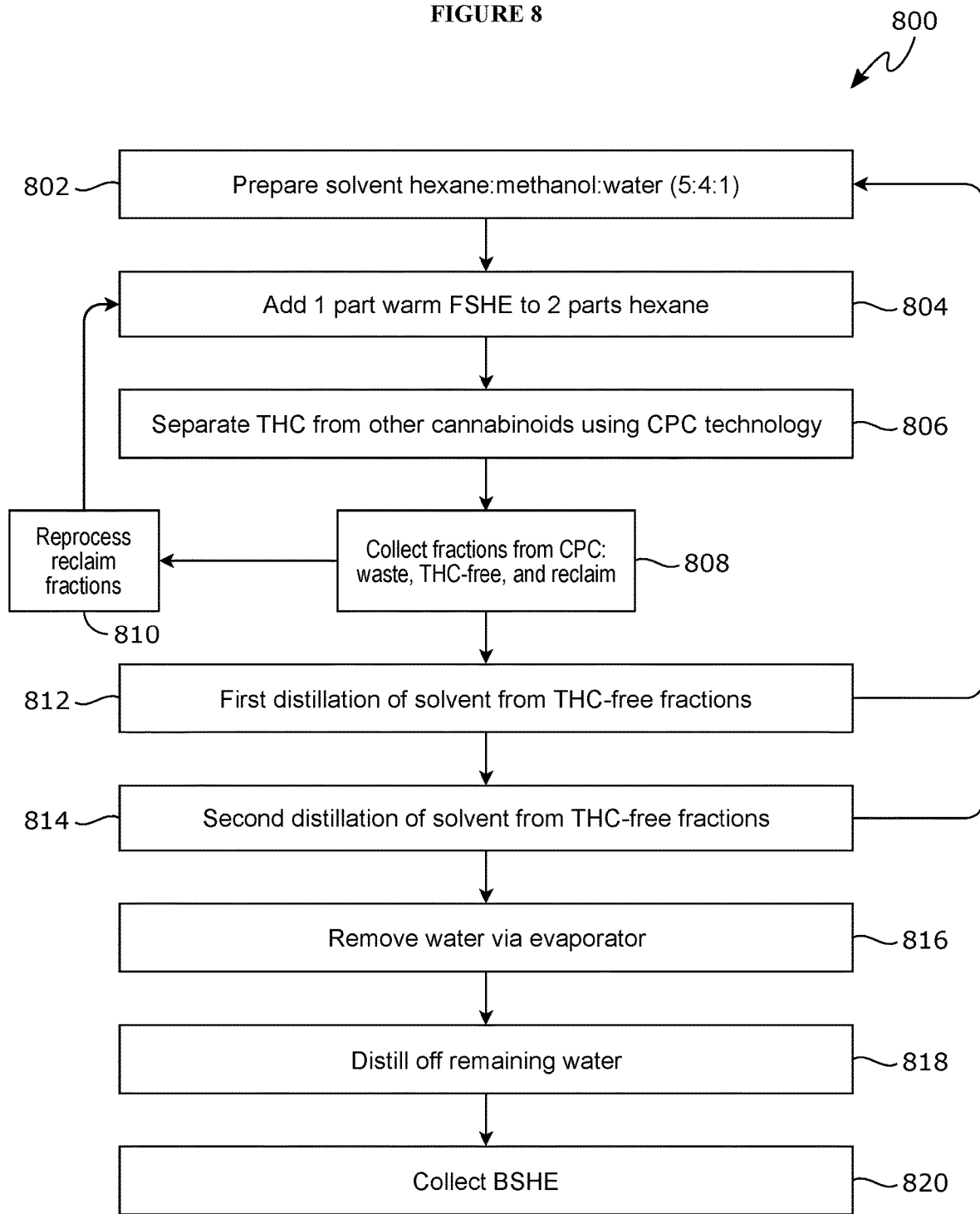
FIG. 8 depicts an exemplary process for removing THC from a FSHE, to produce a broad spectrum hemp extract (BSHE).

After much experimentation, we discovered a multi cannabinoid extraction and purification process that, at a minimum, decreased cost and waste while improving throughput, yield, consistency of results, and the variety of cannabinoids retained in the purified extract. FIG. 1 is an overview of an improved process (1) for producing a FSHE, and FIG. 2 is a block diagram of a system (200) on which the process (1) may be performed. Generally, the process (1) includes the following steps and associated system (200) components: preparing hemp GM for extraction (2, 202), extracting soluble materials/substances from the prepared GM (3, 206), distilling the extraction solvent to concentrate the extract (4, 210), partitioning the concentrate into two phases based on solubility characteristics (5, 212), distilling the nonpolar solvent from the upper phase of the partitioned concentrate to obtain a crude oil (6a, 214), decarboxylating and degassing the crude oil (6b, 216), and refining the crude oil to obtain a FSHE (7, 218). The FSHE may undergo optional additional process (FIG. 8) such as to produce a BSHE. The particulars of each of the forgoing steps are addressed in the ensuing paragraphs and associated figures.

Preparing the GM begins with the grower. Specifically, it starts with the seeds planted and continues through harvest and packing. Plants used to produce the hemp extracts detailed herein are recognized by the United States Department of Agriculture (USDA) as "hemp" having less than 0.3% w/w THC. Moreover, the harvested source material should have less than 0.01 ppm pesticides and, after drying, a sustained water activity (a w) of less than 0.8, and preferably less than 0.7 to prevent mold growth. To assist growers in providing the best product possible, experiments were conducted emulating packing and/or weather conditions experienced by many growers. Generally, source material was packed at different rates and access to fresh air was controlled to mimic actual packed source material in barns. For the best results, it was found that source material should dry to have an a w below 0.8 before packing. Once the a w is below 0.8, mold growth is not observed when packed. Drying to have an a, below 0.8 took about 24 hours at room temperature if source material is loosely packed.

Weather may also affect source material a w especially if hung in barns and threshed. From experiments designed to test hemp source material a w in wet weather, it was determined that one or two days of rain did not detrimentally affect the a w of the source material as it hung in a barn, but continuous rain over a few days raised the a w above acceptable limits, increasing susceptibility to mold growth. With the forgoing in mind, growers may plan for optimal growing, harvesting, and packing of source material to initially obtain an acceptable a w and to maintain that a w while the source material is in their hands.

Figure 3:
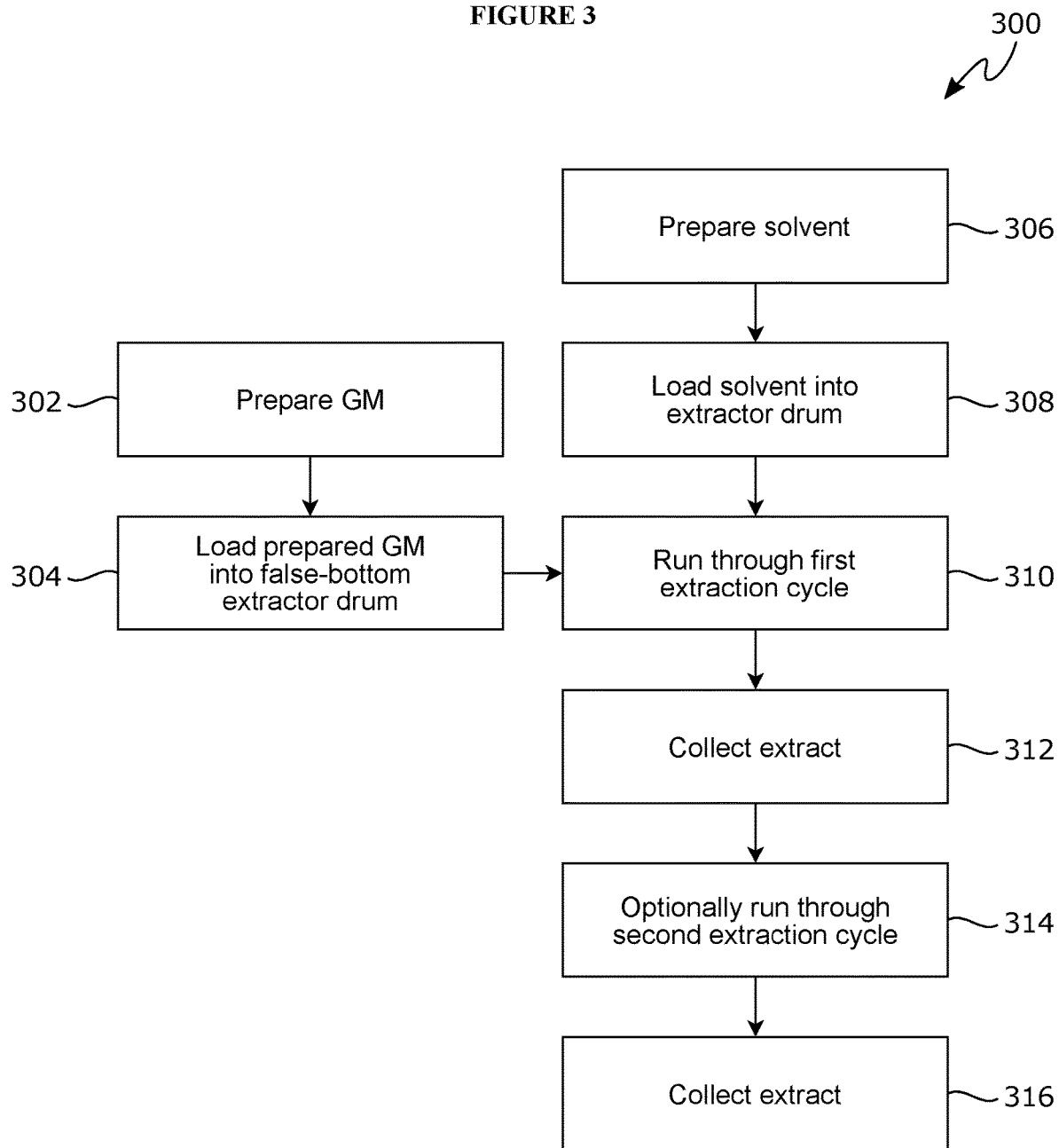
FIG. 3 depicts a flow diagram of the step for extracting substances from hemp green material.

Overall yield depends not only on the quality of the source material, but also upon the degree to which the desired molecules are removed from green material (GM) and retained without loss. Green material prepared for extraction generally refers to the parts of the hemp plant that produce the most cannabinoids such as flowers/inflorescence and leaves. The steps of preparing hemp GM (2) and extracting substances (3) from the hemp GM are detailed in method (300), which is outlined in FIG. 3. The method (300) may include inspecting the GM from the grower (302) before extraction such as by visual inspection for mold or other infestations and by testing, if not previously done. For example, the GM is tested to ensure that it contains less than 0.3% w/w THC and less than 0.01 ppm pesticides, and that is has an a w below 0.7. Dried GM is chopped/ground to about 0.25 inches and weighed to a predetermined weight. Also referring to FIG. 2, the prepared GM is loaded (304) into an extractor drum (206) via a box dumper and auger conveyer (202). During loading, the prepared GM may need to occasionally be tamped down to fit the entire predetermined weight into the extractor drum (206). The extractor drum (206) is fitted with a mesh screen (208) to create a false bottom and to help keep particulate GM from the extraction solvent that collects at the bottom of the extractor drum (206).

The extraction solvent is also prepared (306) before use by cooling it to a temperature at or below freezing. Generally, the extraction solvent is cooled in a solvent tank (204) having a jacket through which a chilled fluid is pumped. In this way, the extraction solvent is chilled to a temperature between about 0° C. and about −20° C. before use. When the extraction solvent is at a desired temperature, it is pumped into the extractor drum (206) until it reaches a desired volume, but at least as much as is needed to saturate the GM within the extractor drum (206). In a preferred embodiment, the extraction solvent is completely denatured alcohol formulation CDA-12A-1 (completely denatured alcohol) from Greenfield Global, which comprises 5% heptane and 95% 200 proof ethanol, although embodiments are not limited thereto.

When the extractor drum (206) is filled with the appropriate amounts of prepared GM and extraction solvent, the GM is run through a first extraction cycle (310). Generally, the extraction solvent flows through the GM and collects in the false bottom of the extractor drum (206). From there, the extraction solvent is pumped back to the top of the extractor drum (206) to percolate through the GM and collect in the false bottom where it is again pumped back to the top of the extractor drum (206). The cycling of the extraction solvent continues for about one hour at atmospheric pressure. Thereafter, the extract from the first extraction cycle is collected (312) by being pumped through a fine mesh filter to remove any particulate GM and into a holding tank.

The GM in the extractor drum (206) may be subject to a second extraction cycle (314), although it is not required. If a second extraction cycle (314) is desired, the extraction drum (214) is filled with cold extraction solvent to a volume that is about ⅓ to ½ of the volume used for the first extraction cycle (310). The second extraction cycle (312) circulates the extraction solvent in the same way as the first extraction cycle for at least about an hour to extract any additional soluble material. If multiple extractions are performed, the extractions from each can be combined from each extraction step. Thereafter, the extract from the second extraction cycle (314) is pumped out to the holding tank and the GM is discarded. The extraction solvent including materials/substances from the GM dissolved therein is generally referred to as the extract. The extract contains all soluble substances extracted from the GM including, without limitation, waxes, sugars, cellulose, chlorophyll, dirt, cellular debris, and of course, cannabinoids and other phytonutrients.

Since the purpose of the extraction step (3) is to extract hemp oils (comprising cannabinoids) from hemp GM, improvements at this stage will improve yield. Thus, the foregoing method for extracting substances from hemp GM was developed by changing certain parameters and examining yield. Since impurities in the black tarry substance seem to contribute to the difficulty in working with the tarry substance, different extraction solvents were examined to see if impurities could be left behind (i.e., not extracted) while maintaining, or preferably increasing, yield. Specifically, yield was examined when hexane, ethanol, and completely denatured ethanol were used as extraction solvents. Hexane produced suboptimal results. When extracting with ethanol, yield was better, and extraction with completely denatured alcohol yield was the best. Furthermore, chilled completely denatured alcohol (as described above) gave the best yield overall even though the black tarry substance remained an issue.

Other parameters were tested to see if their effect on yield. Surprisingly, the size of prepared GM influenced outcome. This is especially true when the size of the GM was considered in combination with the false bottom of the extractor drum (206). Again, in an effort to keep as much debris, impurities, and other contaminants out of the extract as possible, filtering the extract through a natural material such as carbon, diatomaceous earth, or sand, was examined as was filtering through one or more synthetic filters. The synthetic filters, such as the one (208) creating the false bottom and or the ones through which the extract is pumped to the holding tanks, sufficiently kept particulate GM out of the extract. Furthermore, it was found that the optimal size of the GM in combination with the synthetic filters is about 0.25 inches. This size allows for complete extraction of desired cannabinoids and other phytonutrients without being so small to generate losses due to fine cutting or grinding, which would also necessitate a more expensive and cumbersome filtering of particulate GM from the extract.

Another parameter examined during extraction redevelopment was the necessity of freezing the GM before extraction. Yields compared from extracts of frozen GM and room temperature GM showed that freezing the GM before extraction does not improve efficiency. The combination of the forgoing results decreased cost and time by omitting a freezing of the GM and filtering the extract through a natural material. It also increased our yield by allowing more quantities and types of cannabinoids to be extracted with completely denatured alcohol. The surprising result, however, was finding that the size of the prepared GM from which the cannabinoids are extracted greatly improved yield.

The next step (4) of production process (1) begins the purification aspect by distilling the extraction solvent from the extract to form a concentrate. The concentrate contains all soluble extracted materials regardless of desirability. In other words, this step primarily removes just the extraction solvent. The removed extraction solvent is collected for reuse whereas the resultant concentrate undergoes additional processing. Referring the FIG. 2, the holding tank (not shown) in which the extract from the previous step is stored connects to an evaporator (210). The evaporator (210) uses plate heat exchange technology to evaporate and condense the extraction solvent. As a result, the condensed extraction solvent is separated from the concentrated extract or concentrate. Referring to the method (400) detailed in FIG. 4 and more specifically, the extract is fed (402) from the holding tank to the evaporator (210), and particularly through a plate heat exchanger at a pressure of between about 5 and 10 psi. Steam is supplied to the plate heat exchanger at a pressure of between about 20 and 30 psi. The steam heats the extract to a temperature above about 160° F. and preferably at about 190° F., which forces the extraction solvent to vaporize (404). A temperature of between about 160° F. and 190° F. must remain fairly constant during extraction solvent vaporization and condensation. Thereafter, vaporized extraction solvent passes through a condenser set at about 70° F. to cause the vapors to condense (406). The condenser liquid can be any source, however, a 50:50 mix of propylene glycol:water is useful for this purpose. The condensed extraction solvent is collected for reuse (408). When little extraction solvent remains, the temperature of the concentrate circulating in the evaporator (210) is allowed to reach between about 240° F. to about 260° F. This temperature causes remaining extraction solvent to vaporize and condense and at least some of the remaining cannabinoids to decarboxylate. The warm concentrate is pumped (410) to a holding tank (not shown). Notably, the heat and condensing components of the evaporator (210) should be set before distillation begins and a backpressure of about 5-10 psi should be applied to the heated plate exchanger to prevent distillation inside the plates. The pressure of the holding tank in which the extract is contained is at atmospheric pressure. After the extraction solvent and concentrate are removed from the evaporator (210), additional ethanol or completely denatured alcohol can be used to remove accumulated concentrate from the evaporator (210).

Figure 5:
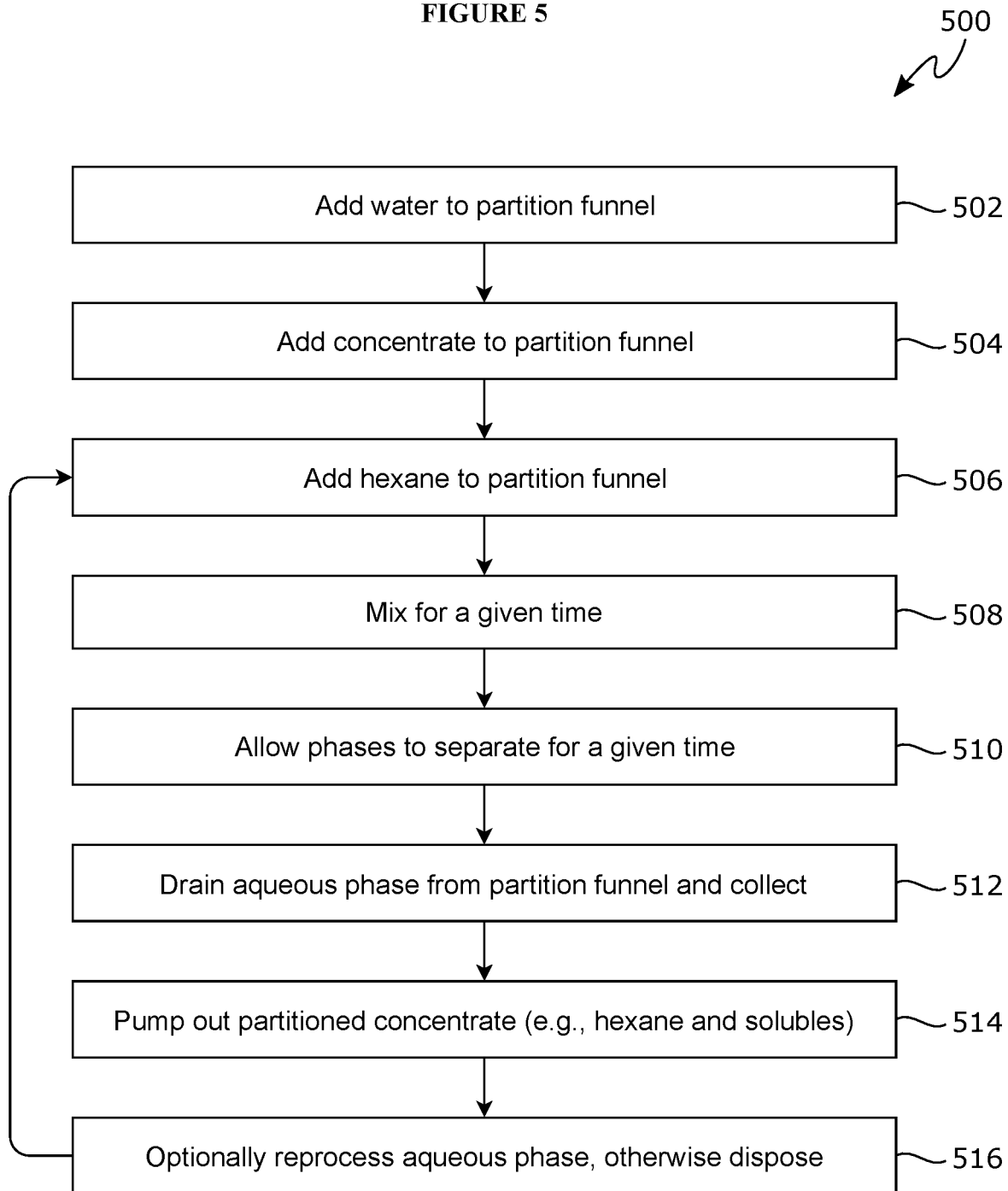
FIG. 5 depicts a flow diagram of the step for partitioning the concentrate between two different liquid phases.

The next step in the process (1), the partitioning step (5), is detailed in the method (500) of FIG. 5. This step was newly created for the purification part of the process (1) and is designed to reduce the difficulty in working with the concentrate, which is the black tarry substance. As water soluble impurities in the concentrate are largely responsible for the difficulty in working with the concentrate, and the attempt to diminish extraction of water-soluble impurities with hexane (directly from GM) did not result in a sufficient yield, experiments were performed to see if water soluble impurities could be removed from the extract without a loss in yield.

Initial experiments focused on liquid/liquid extraction using water and hexane on the extract, which includes the extraction solvent. The idea behind liquid/liquid extraction being that hydrophobic materials/substances will dissolve and separate from hydrophilic materials, which could be removed with an aqueous phase. After testing various ratios of hexane, extract, and water, it was found that the best ratio for separating components in 2 phases without loss of yield was 5:1:1 (hexane:extract:water). This ratio also made purification at a subsequent distillation step much easier and overall cleaning faster and easier. An optimal time need for phase separation was also determined.

Figure 4:
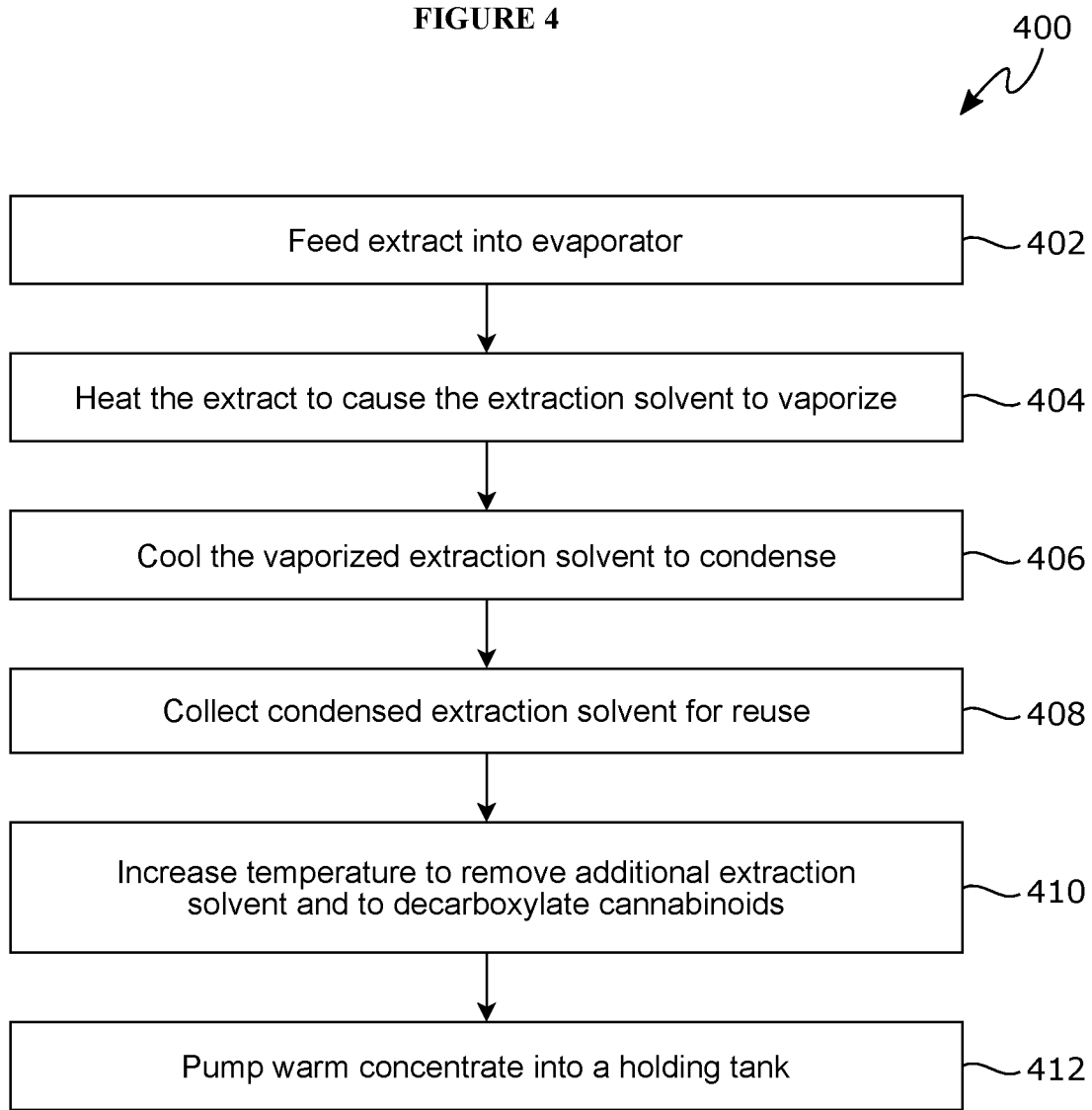
FIG. 4 depicts a flow diagram of the step for distilling extraction solvent from an extract to concentrate the extract.

With continued experimentation, it was discovered that better results were achieved when the extraction solvent was removed (e.g., step 4 FIG. 1; FIG. 4, 400) before the liquid-liquid extraction. Namely, it was found that when partitioning the extract, CBDA gravitated to the aqueous phase and was being removed with the water-soluble impurities. CBDA is the precursor to CBD, thus its retention is paramount to yield. Several unexpected advantages came with removing the extraction solvent before partitioning. One was that the extraction solvent could be recovered and reused instead of disposing of it as waste. As a consequence, the waste produced by partitioning was cleaner being primarily water, which also decreases cost of disposal. More importantly, however, was the realization that the heat from the evaporator (210) causes CBDA to decarboxylate to CBD. Since CBD dissolves more readily in hexane than in water, when more CBD is generated (due to the decarboxylation of CBDA) going into the partition step, yield dramatically increased. Thus, to ensure that CBDA is decarboxylated to CBD, the previous step (step 4/FIG. 4), was modified to force decarboxylation of CBDA (410). Specifically, circulating the concentrate in the evaporator (210) at temperatures at about 240° F. to about 260° F. will cause at least a portion of extracted CBDA to decarboxylate. Another advantage of removing the extraction solvent before partitioning is that more concentrate than extract can be added for each batch partitioned due to the loss of extraction solvent volume. In turn, less time and energy are spent on the partitioning step.

Since the concentrate is more suitable to partitioning than the extract, solvent ratios and other parameters also had to change. For example, to get the best yields, it was discovered that there is a certain sequence in which the solvents and concentrate should be mixed, time needed for the phases to separate, and that the aqueous phase could be collected and repartitioned. Additionally, it was found that the connection between the evaporator (210) and the partition funnel (212) could be flushed with ethanol, which can be added to the partition funnel (212) for even more cannabinoid recovery.

Referring to FIG. 2 and FIG. 5 together, potable water is added to the partition funnel (212) before anything else (502). There should be enough water so that the final ratio of water to concentrate to hexane optimally is 1 part water, 2 parts concentrate, and 2 parts hexane. There is flexibility, however, such that hexane may range from about 2 parts to 5 parts, concentrate may range from about 2 parts to 5 parts and water may range from about 1 part to 5 parts. Thereafter, concentrate is pumped from the evaporator (210) to the partition funnel (212, 504). The concentrate and water should mix as the concentrate is pumped into the partition funnel (212). Thereafter food grade hexane (98% pure) is added to the partition funnel (506). The partition funnel is set to circulate the hexane, concentrate, and water at atmospheric pressure for between 1 and 20 minutes, and preferably between 5 and 10 minutes (508). A longer run time is acceptable, but not necessary. Circulating allows the phases to mix and for the extracted materials to dissolve in either the aqueous phase or the hexane phase. For example, water soluble impurities such as sugars, cellulose, chlorophyll, and the like will dissolve in water and hydrophobic materials such as oils (e.g., containing cannabinoids), waxes, and the like will dissolve in hexane. After mixing, the two phases (i.e., hexane/hydrophobic, and water/aqueous) should separate after about 60 minutes (510). A longer duration may be used but is not necessary. A shorter duration for separation may be effective, but risks losing some of the yield.

After the phases have separated, the water (and water-soluble material) is drained into a holding container (512). The hexane layer with soluble material dissolved therein is pumped (514) to the falling film evaporator (214). Optionally, for example if the separation of the two phases was not clear, the collected water may be repartitioned by adding it back into the partition funnel (212) and reprocessing. For the second partition process, however, an equal amount of hexane and water are added to the partition funnel (212) before repeating the partitioning. Repartitioning the aqueous phase may increase cannabinoid yield, especially if CBDA was not fully converted to CBD via evaporator (210). The second partition may recover any CBDA that may have been lost in the aqueous phase. As mentioned, the connection from the evaporator (210) to the partition funnel (212) may be flushed with a small amount (e.g., 5 liters) of ethanol, which can be added to the contents of the partition funnel soon after the concentrate is added to the partition funnel (504, 506). The ethanol will separate out with the aqueous layer without affecting yield.

The addition of the partitioning step (5) to the purification process tremendously increased throughput by diminishing the extensive cleaning time from about two weeks to less than 3 hours. It also increased throughput by rendering a cleaned partitioned concentrate that did not need extensive cleaning thereafter. This step (5) also improved a capacity constant by improving the flow and reducing the cleaning time. Equipment was capable of more up-time thus improving capacity without added complexities and hours of operating. The most significant benefit obtained by including the partitioning step (5) into to the overall process was increase in yield; quantities of FSHE were greater than before and cannabinoids in the FSHE previously lost were now retained. That is, without this step (5) only about 50-70% of cannabinoids were recovered; with this step (5) there is a 30% increase of cannabinoid recovery. See, e.g., Table 2.

Figure 6:
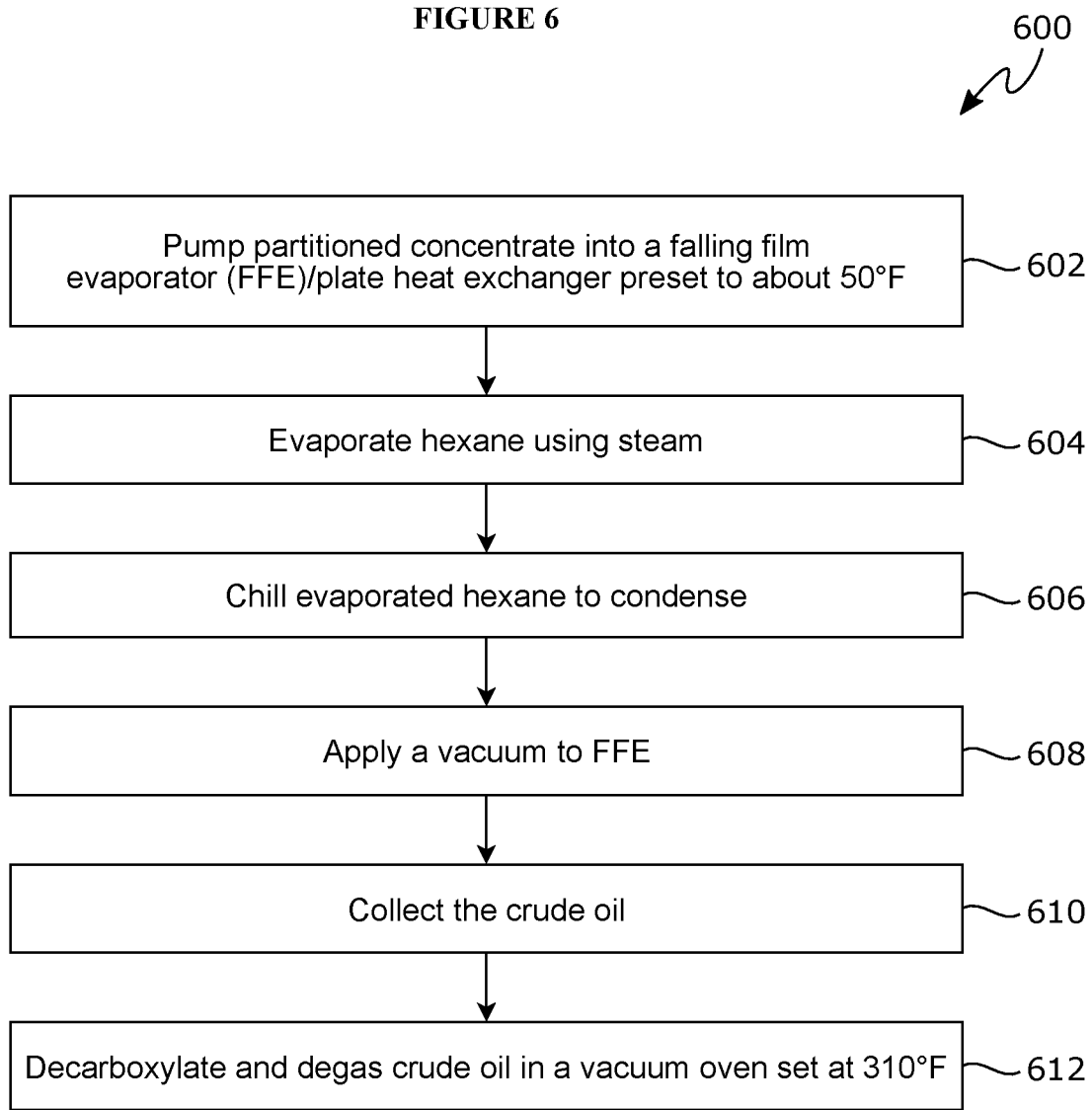
FIG. 6 depicts a flow diagram of the step for distilling a nonpolar solvent from the partitioned concentrate, which results in a crude oil.

The overall process (1) was further modified to remove hexane from the partitioned concentrate. Generally, hexane is removed via distillation (6a). In an embodiment, hexane is vaporized in an evaporator such as a falling film evaporator (214) and condensed via plate heat exchanger. Hexane removal from the partitioned concentrate results in a crude oil. The step (6a) of removing hexane from the partitioned concentrate is detailed in the method (600) of FIG. 6. To ensure hexane vapors condense properly, a chiller is turned on and set to about 50° F. before the partitioned concentrate is pumped (602) to the falling film evaporator (214). The heating element of the falling film evaporator (214) applies steam to heat the partitioned concentrate to a temperature of from about 160° F. to about 200° F., until the hexane vaporization occurs (604). The steam amount is adjusted to ensure that the chiller compressor operates at less than 100% and preferably at 60%. Hexane vapors condense (606) via the plate heat exchanger, which utilizes chilled water to reduce hexane vapor temperature. The partitioned concentrate cycles through this system until hexane is completely distilled based on visual assessment. While cycling, the evaporation temperature can reach as high as about 275° F. The chilled water, however, should not rise more than a few degrees about the 50° F. set point. Thus, the steam to the evaporator should be monitored and adjusted accordingly.

Once the hexane has visually stopped distilling, a vacuum may be applied to the system (608). Generally, the vacuum will remove any remaining hexane that was not removed via distillation at atmospheric pressure. Steam flow to the evaporator (214) is decreased and a low pressure vacuum is applied (e.g., <10 torr). Pressure is gradually increased to between about 20 and 25 torr. Steam flow may also be increased if possible. Hexane distillation under vacuum continues for about an hour. Thereafter, the resultant crude oil is pumped out for degassing in a vacuum oven (610, step 6b).

The vacuum oven (216) reduces the pressure even more than that of the falling film evaporator (214), which evaporates residual solvent from the crude oil. The temperature in the vacuum oven is set to about 310° F. and the vacuum is set to less than 2 torr. At this temperature and pressure, trace solvents are evaporated off of the crude oil. Moreover, carboxylic acids, including cannabinoids in their carboxylic acid forms are decarboxylated, if not already decarboxylated at a prior step. Certain light terpenes may also evaporate in the vacuum oven (216). Crude oil is left in the vacuum oven until visual bubbling has stopped (612). Typically, this is from between 1 minute to 6 hours, and preferably, for less than about 3, 2, or 1 hour. Degassing in the vacuum oven is also a step newly developed for the purification process. Before adding this step (6b), degassing occurred during subsequent distillation. It was found that degassing before subsequent distillation improved yield. Moreover, degassing during subsequent distillation potentially allowed heavy metals to escape into the final product, which is a source of unacceptable contamination. Thus, degassing (step 6b) in the vacuum oven (216) has at least a twofold benefit: increased yield and decreased contamination of the end product.

After degassing (6b), the crude oil is ready for refining (7). Refining removes any remaining impurities such as chlorophyll, solvents, heavy metals, and the like. Refining is accomplished by at least one, preferably two, and optionally three passes through a wiped film short path still (218). The first pass separates volatile compounds such as terpenes from the crude oil and the second pass separates cannabinoids from less volatile impurities. If desired, impurities collected from the second pass may be subjected to a third pass to evaporate and separate any remaining cannabinoids from the impurities. Still parameters are adjusted for each pass to obtain optimal results. See Table 1, below.

Generally, to refine a substance in the wiped film short path still (218), the substance may be heated before or as it enters a head of the still (218). The still wall is heated by either a heated jacket or electrically. Heating causes the substance to flow into the still (218) to run down the inside of the wall. As the substance runs down the wall, it spreads into a thin layer by rotating wipers. The still (218) is also kept under a vacuum. Thus, the heat and the vacuum cause volatile components to evaporate and condense against an internal condenser. The condensate at the internal condenser is a distillate. Whatever has not evaporated and condensed exits the still (218) as a residue. Both the distillate and the residue may be collected. In an embodiment, the still may be connected to an external condenser (not shown) which will condense vapors that have flowed upward and out of the top of the still. If vapors pass the external condenser, they may condense in a cold trap that lies between the external condenser and a vacuum pump. Parameters for each pass of the wiped film short path still (218) are as follows:

For the second pass distillation, the still is heated to a higher temperature and is set at a lower pressure (Table 1) since the higher pressure terpenes have already been removed in the first pass. The internal condenser is also at a higher temperature (Table 1). These changes to still parameters force cannabinoids to evaporate and condense inside the still leaving behind heavier, less volatile impurities. That is, within the still, cannabinoids evaporate from the first residue and condense on the internal condenser to flow out of the still as the second distillate (710). The heavier, less volatile materials do not evaporate and exit the still as a second residue (712). The second distillate is a refined oil comprising a FSHE, which is collected. Any cannabinoids remaining in the second residue may be extracted via an optional third pass through the same still or a sequential still.

Before running the second residue through a third pass distillation, the second residue is mixed with canola oil (714) in a ratio of 10:1 (second residue: canola oil) to thin the second residue for easier distillation. On the third pass through the still, the feed is pre-warmed to a higher temperature and the still is heated at a slightly warmer temperature as comparted to the second pass through the still (see Table 1). The remaining settings are essentially the same as with the second pass. During this third pass (716), any remaining cannabinoids evaporate and condense against the internal condenser to be collected as the third distillate (718) which is an oil comprising FSHE and the third residue is collected to be disposed of as waste (720).

The third distillate is added to the second distillate as they are both refined oil comprising FSHE extracted from the same starting materials (716). Generally, the second distillate and third distillate are passed to a heated tank (220) where they are mixed into a homogenous mixture and collected into glass jars for quality testing. An independent lab tests the FSHE for pesticides, heavy metals, microbes, residual solvents, and mycotoxins. The independent lab also provides a cannabinoid profile determined by liquid chromatography diode array detector (LC-DAD). An exemplary cannabinoid profile resultant from the forgoing extraction and purification process (1) is summarized in Table 2.

TABLE 1

WIPED FILM SHORT-PASS STILL PARAMETERS

| | Heater (° C.) | Internal Condenser (° C.) | External Condenser (° C.) | Vacuum gas trap (° C.) | Pressure (Torr) | Infeed Temperature (° C.) | Wiper Blades (RPM) |
|---|---|---|---|---|---|---|---|
| First Pass | 150 | −15 to −5 | −15 to −5 | −95 to −85 | <2 | 60 | 260-300 |
| Second Pass | 170-185 | 70-90 | −15 to −5 | −95 to −85 | <500 mTorr | 60 | 260-300 |
| Third Pass | 180-190 | 70-90 | −15 to −5 | −95 to −85 | <500 mTorr | 80 | 260-300 |

Figure 7:
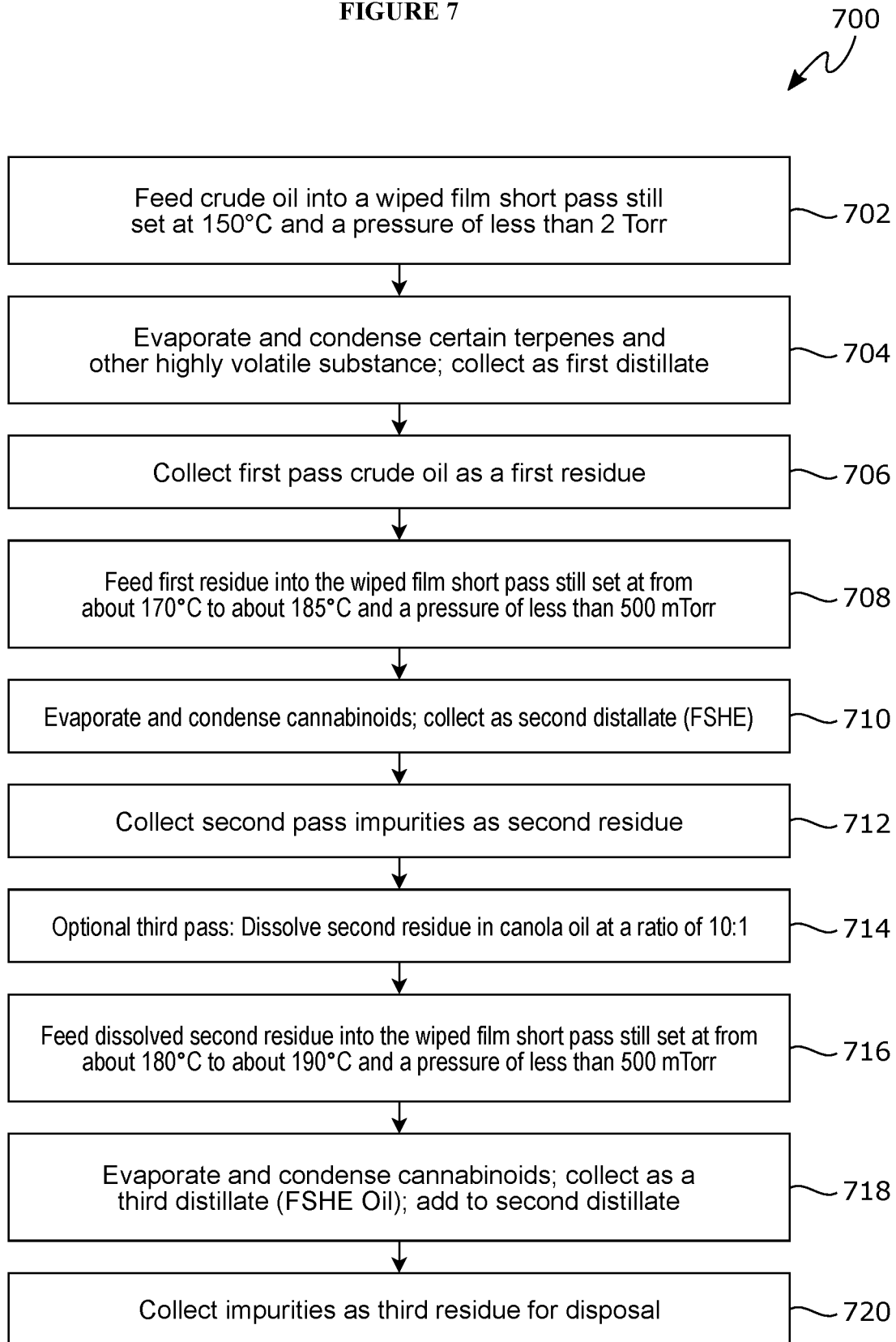
FIG. 7 depicts a flow diagram of the step for refining the crude oil to produce the FSHE.

Referring to FIG. 7, the first pass through the still (218) is called the "terpene pass" because certain terpenes and other highly volatile molecules are removed during this pass. When crude oil is fed (702) into the still (218) that set as indicated in Table 1, terpenes, some impurities, and the like evaporate and condense as the "first distillate" (704). What has not evaporated and condensed is the first residue, which is a more refined crude oil. The first residue is collected (706) and may optionally be dissolved in canola oil (10:1) before being run through a second distillation (708) on the same still or a sequential still.

TABLE 2

EXEMPLARY CANNABINOID PROFILE OF FSHE AS DETECTED BY LC-DAD

| Cannabinoid | mg/g | % |
|---|---|---|
| $\Delta^8$-THC | ND | ND |
| $\Delta^9$-THC | 25.47 | 2.547 |
| $\Delta^9$-THCA | ND | ND |
| THCV | ND | ND |

TABLE 2-continued

EXEMPLARY CANNABINOID PROFILE OF
FSHE AS DETECTED BY LC-DAD

| Cannabinoid | mg/g | % |
|---|---|---|
| THCVA | ND | ND |
| CBD | 799.43 | 79.943 |
| CBDA | ND | ND |
| CBC | 18.89 | 1.889 |
| CBCA | ND | ND |
| CBDV | 7.79 | 0.779 |
| CBG | 16.70 | 1.670 |
| CBGA | ND | ND |
| CBN | 1.65 | 0.165 |
| Total THC | 25.47 | 2.547 |
| Total CBD | 799.43 | 79.943 |
| Total Cannabinoids | 869.94 | 86.994 |
| Sum of Cannabinoids | 869.94 | 86.994 | where ND means not detected; total THC = $\Delta^9$-THC + (0.877 × $\Delta^9$-THCA); total CBD = CBD + (0.877 × CBDA); and total cannabinoids = Σ(neutral cannabinoids) + [0.877 × Σ(acidic cannabinoids)]

Notably the cannabinoid profile shown in Table 2 is a profile from an actual FSHE production lot. Quantities and types of cannabinoids in a particular production lot may differ. Even so, most FSHE lots have a profile that is similar to that shown in Table 2 with quantities ranging from about ±25% of the quantities listed in Table 2 for minor elements (below 5% by weight, and ±10% for the major component, CBD. Moreover, it is not unusual to extract and recover small amounts of other cannabinoids such as THCV and CBL, which may be included at up to 2.5% each.

In certain applications, the FSHE is desired; other applications, however, require a $\Delta^9$ THC-free hemp extract. Thus, the FSHE produced by the extraction and purification method (1) may be further processed to produce a BSHE, which is Δ9 THC-free, meaning below the level of quantitation. Other aspects of a B SHE, such as the cannabinoid profile, are substantially similar to the FSHE from which it was produced.

The primary steps for producing BSHE from FSHE include (i) separating THC from other cannabinoids using Centrifugal Partition Chromatography (CPC), and (ii) distilling solvent from THC-free fractions obtained via CPC. These steps are detailed in FIG. 8 as process (8).

CPC is a type of chromatography that uses two liquids, one as a stationary phase, and the other as a mobile phase. The stationary phase is immobilized by a strong centrifugal force and the mobile phase moves through the stationary phase to separate different molecules. This technique typically requires a two-phase mixture of solvents. Different compounds can be separated based on the components of the particular solvent system and the partition coefficients of the molecules in the selected solvent system. Thus, by using two different solvents together with CPC, similar substances can be separated. Generally, using CPC, as one liquid is introduced into the machine, another exits from the CPC machine. Molecules having different partition coefficients will come off of the CPC machine at different times and/or in different fractions due to separation through the stationary phase in the CPC machine.

The solvent system used to separate THC from other cannabinoids includes a nonpolar solvent (e.g., hexane) and two polar solvents (e.g., methanol and water). The ratio of these solvents is important as is the density of the non-polar solvent mixture. For freshly prepared (802) solvents, the ratio of hexane to methanol to water is 5:4:1. Per the BSHE production process (800) solvents can be reused (812, 814 to 802). Nevertheless, the ratio of the solvents (5:4:1) should be maintained for proper THC separation. Generally, collected used solvents are allowed to separate in a container where they will form an upper layer that is primarily hexane, and a lower layer that is primarily water and methanol. After separation, the two layers are transferred to respective containers. The density of the lower phase is adjusted by adding water and/or methanol (as indicated by the particular instance) until the density is about 0.852 g/cm³ at 70° F.

To prepare FSHE for CPC separation, the desired amount of FSHE is warmed in an oven until it is fully dissolved. The warmed FSHE is added to the upper phase (e.g., hexane) such that the ratio of hexane to FSHE is about 2:1 (804). The FSHE should be completely dissolved in the hexane before being loaded into the CPC machine. At this point the solvents and sample are ready to load into the CPC machine.

In brief, the CPC machine is filled with clean upper phase mixture of water and methanol and the centrifuge within the CPC machine starts rotating. Thereafter, the FSHE dissolved in hexane is loaded into the CPC machine and allowed to separate (806). Additional lower phase is added during FSHE separation. Thereafter upper phase is added to the CPC machine. Meanwhile, fractions coming off of the CPC machine are collected (808). Fractions can be monitored via a UV absorbance spectrum. At the beginning and the ending of a CPC run, where cannabinoids are not expected to come off the machine, the UV absorbance spectrum is low. In contrast, the presence of cannabinoids will cause the UV absorbance spectrum to show high points. This absorbance spectrum lets an operator of the CPC machine know when cannabinoids are coming through the system. Cannabinoids without THC have a different absorbance spectrum than those with THC, so it is possible to estimate which fractions are THC-Free and which are not. Thus, per the solvent system, sample loading, and CPC parameters, fractions can be divided into three categories: Waste, THC-free, and Reclaim. Simplified parameters of the CPC run method are outlined in Table 3. Since non-THC cannabinoids (e.g., CBD) dissolve better in the lower phase than THC, they come off the CPC machine first. Conversely, as THC dissolves better in the upper phase, it will come off the CPC machine later in the process. Reclaim is a mix of THC and CBD that can be separated in a second pass through the CPC.

TABLE 3

TIME, INPUT, OUTPUT, AND FLOW PARAMETERS
FOR AN EXEMPLARY CPC RUN

| Time (min) | Input Source (% Infeed) | Fraction/Output Type | Flow (mL/min) |
|---|---|---|---|
| 0 | 100 Lower Phase | Waste | 250 |
| 0.2 | 100 Sample | Waste | 150 |
| 1.5 | 100 Lower Phase | Reclaim | 250 |
| 6 | 100 Lower Phase | THC-free | 250 |
| 12 | 100 Lower Phase | Reclaim | 250 |
| 13 | 100 Upper Phase | Reclaim | 250 |
| 16 | 100 Upper Phase | Waste | 250 |

Before Reclaim fractions can be rerun on the CPC, the solvent is first removed by one or more distillation processes (810). As a nonlimiting example, Reclaim fractions may have solvent distilled off in the falling film evaporator (214), the wiped film short pass still (218), or both. These distillations are essentially the same as was described for FSHE purification. Thereafter, the resultant oil (e.g., Reclaim oil) may be rerun in the CPC machine. The run of Reclaim oil is similar to that of the initial run except that the ratio of hexane to Reclaim oil is 2.5 (hexane) to 1 (Reclaim oil) and only two fractions collected: THC-Free and Waste.

Before continuing with removal of solvent, THC-Free fractions are internally verified to be truly THC-Free. If not, the fractions can be rerun through the CPC (e.g., as Reclaim fractions) and reverified as being THC-Free. The THC-Free fractions are combined for solvent removal via a horizontal wiped film evaporator.

To remove methanol from the THC-free fractions using the horizontal wiped film evaporator (812), a heating jacket is set to heat the evaporator from about 60° C. 100° C., or higher, so long as below methanol's flash point, and at full vacuum, which is about 100 torr. As the THC-free fractions move into the evaporator, they are spread into a thin layer by the wipers, to enhance solvent (e.g., methanol) evaporation. The solvent vapors move to the condenser, which is set at 4° C. to condense the vapors back to liquid solvent. As was previously mentioned, the distilled solvent can be reused in the CPC. After about 4 hours, the undistilled portion containing concentrated THC-Free cannabinoids is collected.

As solvent may still be present in the concentrated THC-Free portion, a second distillation is performed on a rotovap evaporator (814), with the bath set to at least about 100° C. under the strongest possible vacuum to distill off the remaining methanol/solvents. Vaporized solvent is condensed by a condenser set to about −20° C.

After the remaining methanol is removed from the concentrated THC-free portion, the contents, which includes water, are allowed to cool for at least 1 hour, but a longer time will not affect yield. Once cooled, water and the THC-Free concentrate can be separated on the evaporator (816). To do so, the vacuum is turned on, but not the heat. The vacuum causes the oil to clump and separate from the water. After being under vacuum for at least 1 hour, water and the THC-Free product should be fully separated. Water is removed from the THC-Free product and the THC-Free product is returned to the evaporator to distill off the remainder of the water (818). For example, at a temperature of about 100° C. and a vacuum pressure of about less than 150 millitorr, water will evaporate away from the THC-Free product. When the THC-Free oil changes from cloudy to clear and there is little to no bubbling of the oil, the water has been distilled off and the THC-Free product, which is a BSHE (820), is sent to an independent lab for testing.

TABLE 4

EXEMPLARY CANNABINOID PROFILE OF BSHE AS DETECTED BY LC-DAD

| Cannabinoid | mg/g | % |
|---|---|---|
| $\Delta^8$-THC | ND | ND |
| $\Delta^9$-THC | ND | ND |
| $\Delta^9$-THCA | ND | ND |
| THCV | ND | ND |
| THCVA | ND | ND |
| CBD | 898.49 | 89.849 |
| CBDA | ND | ND |
| CBC | ND | ND |
| CBCA | ND | ND |
| CBDV | ND | ND |
| CBG | 17.14 | 1.714 |
| CBGA | ND | ND |
| CBN | 1.65 | 0.165 |
| Total THC | ND | ND |
| Total CBD | 898.49 | 89.849 |
| Total Cannabinoids | 915.63 | 91.563 |
| Sum of Cannabinoids | 915.63 | 91.563 | where ND means not detected; total THC = $\Delta^9$-THC + (0.877 × $\Delta^9$-THCA); total CBD = CBD + (0.877 × CBDA); and total cannabinoids = Σ(neutral cannabinoids) + [0.877 × Σ(acidic cannabinoids)]

Notably, the cannabinoid profile shown in Table 4 is a profile from an actual BSHE production lot. Quantities and types of cannabinoids in a particular production lot may differ. Even so, most BSHE lots have a profile that is similar to that shown in Table 4 with quantities ranging from about ±10% of the quantities listed in Table 4. Moreover, it is not unusual to extract and recover small amounts of other cannabinoids such as CBC, CBG, and CBL.

Table 5 below provides an acceptable variance for elements within the BSHE.

TABLE 5

BSHE

| Cannabinoid | mg/g | % |
|---|---|---|
| $\Delta^8$-THC | ND | 0-1 |
| $\Delta^9$-THC | ND | 0-0.1 |
| $\Delta^9$-THCA | ND | 0-0.3 |
| THCV | ND | ND |
| THCVA | ND | ND |
| CBD | 900 | 70-99 |
| CBDA | ND | 0-2.5 |
| CBC | ND | 0-3.5 |
| CBCA | ND | 0-5.0 |
| CBDV | ND | 0-2.5 |
| CBG | 15 | 0.1-3.5 |
| CBGA | ND | 0-3.5 |
| CBN | 2.0 | 0.01-0.5 |
| Total THC | ND | 0-1.5 |
| Total CBD | 898.49 | 70-99 |
| Total Cannabinoids | 915.63 | 71-99 |
| Sum of additional Cannabinoids | 0 | 0-10 |

Table 6 below provides an acceptable variance for elements within the FSHE.

TABLE 6

FSHE

| Cannabinoid | mg/g | % |
|---|---|---|
| $\Delta^8$-THC | ND | 0-3.0 |
| $\Delta^9$-THC | 25 | 0.01-5.0 |
| $\Delta^9$-THCA | ND | 0-1.0 |
| CBD | 800 | 65-98 |
| CBC | 19 | 0-3.5 |
| CBDV | 8 | 0-2.5 |
| CBG | 17 | 0.1-3.5 |
| CBN | 1.65 | 0-0.5 |
| Total THC | 25.47 | 0.3-5.0 |
| Total CBD | 799.43 | 65-98 |
| Total Cannabinoids | 869.94 | 65-99.9 |
| Sum of additional Cannabinoids | 0 | 0-10.0 |

A simplified approach to the formulations is that the BSHE includes between 60-95% of a CBD, Δ9-THC of 0-0.1%, but preferably not detectable, and additional cannabinoids between 0.1 and 20%. Whereas, the FSHE includes 0.01 to 5% THC, but preferably between and 0.3 as required in certain jurisdictions. Additional elements include between 0.1 and 20% of waxes and fatty acids.

Either of the BSHE or FSHE once made, can now be utilized in a number of ways. Unfortunately, each of the BSHE and FSHE have a bitter flavor for oral mucosal or oral dosing, and so it is optimal to add the BSHE or FSHE to a suitable oral carrier for such dosage forms. Oils such as long chain triglyceride (LCT) oils or medium chain triglyceride oils (MCT) oils are readily available. In a preferred embodiment, the FSHE is added v/v into a mixture of cold pressed hemp seed oil, coconut oil, or combinations thereof. This makes the resulting oil palatable for oral administration. Typically, the FSHE is added at about 1-10% v/v with cold pressed hemp seed oil and the MCT oil (e.g., coconut oil) each at between 10 and 99% v/v. A flavoring can be added at about 0.1% to 5.0% v/v. Flavors include well known examples including but not limited to citrus flavors, fruit flavors, mint or wintergreen, and the like, which may be natural or synthetic.

In certain embodiments, the FSHE or BSHE can be added to the carrier at up to 99% of the total volume or weight of the composition, inclusive of all ranges from 1-99%.

A preferred embodiment is made by combining the BSHE or FSHE w/w into a mixture of cold pressed hemp seed oil and an MCT oil, and further comprising a terpene blend. In other embodiments, the BSHE or FSHE are added only to an MCT oil, or only to a cold pressed hemp seed oil. In preferred embodiments, a composition comprises between 40 and 70% cold pressed hemp seed oil, and between 30 and 50% MCT oil, and between 1 and 20% of a BSHE or FSHE. More preferably, the embodiment further comprises a terpene mix or other mixture to improve the profile of the composition.

In certain embodiments, a terpene blend is included at between 0.1 and 2.0 v/v. A particular blend may comprise one, two, three, or more terpenes. A terpene blend may include β-myrcene, β-caryophyllene, linalool, α-pinene, citral, D-limonene, and/or eucalyptol. A particular terpene blend comprises a terpene profile including β-myrcene at 15-25%, β-caryophyllene at 15-25%, linalool at 5-15%, α-pinene at 5-15%, citral at 15-40%, D-limonene at 10-30%, and eucalyptol at 0.1-5%. In preferred embodiments, the terpene blend includes at least one, two, three, four, five, six or all seven of the recited seven terpenes. Preferably, the range of each of the terpenes is from between about 0.1% to about 50% of the total volume of the terpene blend. Most preferably, the terpene blend comprises at least 5 terpenes with each terpene representing a concentration of no more than 40% of the total volume of the terpene blend.

A composition comprising the FSHE, cold pressed hemp seed oil, coconut oil, and a terpene blend is optimized for use as a tincture for oral administration. In preferred embodiments, a flavor is further added at between 0.1% to 2.0% v/v of the composition. Such application is provided for sublingual application wherein the FSHE and cannabinoids are intended for uptake through the oral mucosa. It is understood that the material is often eventually swallowed and that additional material is taken through the rear of the mouth, the esophagus as well as into the stomach and undergoes first pass metabolism. In certain embodiments, the FSHE is replaced by a refined BSHE. In further embodiments, the compositions may be formulated into a softgel, wherein the gel coating is produced to form as a dissolvable shell around a quantity of the composition. Such manufacture is well understood by one of ordinary skill in the art. In further embodiments, the composition is admixed into gelatin or another carrier, with the addition of one or more excipients, including but not limited to a flavorant, a sweetener, a color, for manufacture of a gummy product.

For topical administration, the carrier may further include an emulsifying agent. In certain embodiments, a fat may be further included, such as shea butter, which can be utilized as the carrier in place of the MCT oil. In such embodiments, the composition comprises FSHE, cold pressed hemp seed oil, a second oil or fat, and optionally a terpene blend. In preferred embodiments, the second oil or fat is shea butter.

In certain embodiments, the FSHE is replaced by a BSHE. Accordingly, a product may comprise between 1 to 50% of a BSHE or FSHE and between 99 and 50% of additional excipients, including the carrier and other components, which is suitable for topical administration.

The oil, whether a BSHE or a FSHE is manufactured and bottled. In a subsequent processing step, the BSHE or FSHE may be encapsulated in a gelatin material for oral administration. Typical soft gelatin capsules comprise between 0.4 and 0.6 mL per capsule of the oils. The manufacture of the gelatin capsule may include further excipients necessary to make the gelatin shell.

A further embodiment is directed towards a mucosal composition. In preferred embodiments, the mucosal composition may be intended for the oral mucosa, the nasal mucosa, the vaginal mucosa, or the rectal mucosa. In preferred embodiments, the mucosal composition is an intravaginal composition. The intravaginal compositions comprises a BSHE or a FSHE at between 1 and 99%, a carrier, preferably a fat or an oil. Additional excipients may be included for stabilizing the formulation and for modifying the flowability or character of the final product. A preferred fat is shea butter. The intravaginal composition may further comprise a terpene blend as detailed herein. In certain embodiments, the pH is modified, for example from a native pH of about 10.5 of the FSHE or BSHE to an acidic pH. An acidic buffer solution, comprising an appropriate conjugate acid and base can be utilized by one of ordinary skill in the art to make the pH acidic, such as between 3.5 and 6, and serve as the pH modifier. Osmolality modifiers may also be utilized, including the addition of salts, such as sodium chloride to the composition. In certain embodiments, a mucoadhesive agent is included, wherein the mucoadhesive agent is chitosan, hydroxyethyl cellulose, methyl cellulose, polyacrylic acid, poly vinyl pyrrolidone, poly vinyl alcohol, poly ethylene glycol, or combinations thereof.

It will be appreciated that the embodiments and illustrations described herein are provided by way of example and that the present invention is not limited to what has been particularly disclosed. Rather, the scope of the present invention includes both combinations and sub combinations of the various features described above, as well as variations and modifications thereof that would occur to persons skilled in the art upon reading the forgoing description and that are not disclosed in the prior art. Therefore, the various methods, formulations, and compositions detailed herein may include one or all of the limitations of an embodiment, be performed in any order, or may combine limitations from different embodiments, as would be understood by those implementing the various methods and systems detailed herein.

What is claimed is:

1. A method for producing a full spectrum hemp (*Cannabis sativa*) extract comprising:
   a. mixing cannabis plant material in an extraction solvent of about 5% heptane and about 95% ethanol cooled to between about −20° C. and about 0° C. and collecting an extract that includes the extraction solvent and soluble substances dissolved therein;
   b. distilling at least a portion of the extraction solvent off of the extract by heating the extract to a temperature of about 160° F. (about 70° C.) to about 190° F. (about 90° C.) and collecting a concentrate that is not distilled off;
   c. removing at least a portion of water-soluble substances from the concentrate by partitioning the at least a portion of water-soluble substances into an aqueous phase and a remainder of substances from the concentrate into a partitioned concentrate dissolved in a phase of a nonpolar solvent;

d. heating the partitioned concentrate to a temperature of about 160° F. (about 70° C.) to about 200° F. (about 95° C.) to evaporate the nonpolar solvent and to yield a crude oil;

e. degassing the crude oil by heating the crude oil to a temperature of at least about 310° F. (at least about 155° C.) in a vacuum that is less than about two torr (less than about 270 Pa), the degassing for a time sufficient to eliminate bubbling of the crude oil, which results in a degassed crude oil;

f. performing a first pass distillation of the degassed crude oil at about 150° C. and collecting a first residue; and g. performing a second pass distillation of the first residue at between about 170° C. and about 185° C., collecting a second distillate that is a full spectrum hemp extract, and collecting a second residue.

2. The method of claim 1 further comprising performing a third pass distillation on the second residue at a temperature of between about 180° C. and about 190° C., collecting a third distillate that is a full spectrum hemp extract, and combining the second distillate of full spectrum hemp extract and the third distillate of full spectrum hemp extract.

3. The method of claim 1 wherein in step (a) the extract is collected by separating the extraction solvent and soluble substances dissolved therein from any of the cannabis-based green material that is not soluble in the extraction solvent and wherein the separating is carried out by filtration.

4. The method of claim 1 wherein partitioning the at least a portion of water-soluble substances into an aqueous phase and a remainder of substances from the concentrate into a partitioned concentrate dissolved in a phase of nonpolar solvent comprises:

c1. adding about 2 to 5 parts concentrate to about 1 to 5 parts water;

c2. adding about 2 parts to about 5 parts nonpolar solvent to the water and the concentrate;

c3. mixing the water, concentrate, and nonpolar solvent for about 1 minute to about 20 minutes;

c4. letting the mixture sit for between 30 minutes and 180 minutes to allow the aqueous phase and the phase of nonpolar solvent to separate; and c5. draining the aqueous phase away from the phase of nonpolar solvent to obtain the partitioned concentrate dissolved in a phase of a nonpolar solvent.

5. The method of claim 4 wherein:

i. the nonpolar solvent is hexane;

ii. the ratio of water, concentrate, and hexane is about 1 part water, 2 parts concentrate, and 2 parts hexane;

iii. the aqueous phase that was drained away is repartitioned in an equal amount of nonpolar solvent; and iv. the nonpolar solvent is collected and combined with the partitioned concentrate dissolved in a phase of nonpolar solvent.

6. The method of claim 1 further comprising adding fresh extraction solvent after removing the extraction solvent to further extract soluble substances from the same green material and combining the extract from each separate extraction step.

7. The method of claim 1 wherein distilling at least a portion of the extraction solvent off of the extract comprises wherein at least 50% of the extraction solvent has been distilled off of the extract, forcing at least a portion of cannabidiolic acid (CBDA) present in the extract to decarboxylate to cannabidiol (CBD) by increasing the temperature to between about 240° F. and 260° F. (between about 115° C. and 130° C.).

8. The method of claim 1 wherein the partitioned concentrate is heated to produce the crude oil in a falling film evaporator and, prior to degassing the crude oil and after visual perception of distillation of the nonpolar solvent has ended, a vacuum of about less than 10 torr (less than 1,350 Pa) is applied to the falling film evaporator for about an hour.

9. The method of claim 1 wherein the degassing step is carried out for between about 1 minute to about 6 hours.

10. The method of claim 1 wherein the first pass distillation is carried out at a temperature of from 145° C. to 155° C.

11. The method of claim 1 further comprising dissolving the first residue, the second residue, or both in canola oil at a ratio of 10 parts residue to 1 part canola oil.

12. The method of claim 1 wherein the concentration of CBD in the second distillate, or the combined second distillate and third distillate, of full spectrum hemp extract is between about 70% and about 90%.

13. The method of claim 1 wherein the concentration of Δ-9-tetrahydrocannabinol (THC) in the second distillate, or the combined second distillate and third distillate, of full spectrum hemp extract is between about 0.1% and 2.99%.

14. The method of claim 1 wherein the total cannabinoids in the second distillate, or the combined second distillate and third distillate, of full spectrum hemp extract is between about 77% and about 97%.

15. The method of claim 1 wherein the second distillate, or the combined second distillate and third distillate, of full spectrum hemp extract comprises at least one terpene.

\* \* \* \* \*